United States Patent
Despres et al.

(10) Patent No.: US 10,849,943 B2
(45) Date of Patent: Dec. 1, 2020

(54) VACCINE COMPOSITIONS COMPRISING AN ATTENUATED MUTANT ZIKA VIRUS

(71) Applicants: INSERM (Institut National de la Sante et de la Recherche Medicale), Paris (FR); Universite de la Reunion Saint Denis, Saint Denis (FR); Institut de Recherche pour le Developpement (IRD), Marseilles (FR); Centre National de la Recherche Scientifique (CNRS), Paris (FR)

(72) Inventors: Philippe Despres, Sainte Clotilde la Reunion (FR); Gilles Gadea, Sainte Clotilde la Reunion (FR); Patrick Mavingui, Sainte Clotilde la Reunion (FR); Wildriss Viranaicken, Sainte Clotilde la Reunion (FR)

(73) Assignees: INSERM (INSTITUT NATIONAL DE LA SANTE ET DE LA RECHERCHE MEDICALE), Paris (FR); UNIVERSITE DE LA REUNION SAINT DENIS, Saint Denis (FR); INSTITUT DE RECHERCHE POUR LE DEVELOPPEMENT (IRD), Marseilles (FR); CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 40 days.

(21) Appl. No.: 16/307,689

(22) PCT Filed: Jun. 22, 2017

(86) PCT No.: PCT/EP2017/065462
§ 371 (c)(1),
(2) Date: Dec. 6, 2018

(87) PCT Pub. No.: WO2017/220748
PCT Pub. Date: Dec. 28, 2017

(65) Prior Publication Data
US 2019/0255125 A1    Aug. 22, 2019

(30) Foreign Application Priority Data
Jun. 23, 2016 (EP) .................................... 16305764

(51) Int. Cl.
| | | |
|---|---|---|
| *A61K 39/00* | (2006.01) | |
| *A61K 39/12* | (2006.01) | |
| *C12N 7/00* | (2006.01) | |
| *C07K 14/005* | (2006.01) | |
| *A61K 39/39* | (2006.01) | |
| *A61K 35/76* | (2015.01) | |
| *A61P 31/14* | (2006.01) | |

(52) U.S. Cl.
CPC .............. *A61K 35/76* (2013.01); *A61K 39/12* (2013.01); *A61P 31/14* (2018.01); *A61K 2039/5254* (2013.01); *C12N 2770/24121* (2013.01); *C12N 2770/24134* (2013.01); *Y02A 50/392* (2018.01)

(58) Field of Classification Search
CPC .. A61K 39/12; A61K 2039/5254; C12N 7/00; C12N 2770/24134; A61P 31/14
See application file for complete search history.

(56) References Cited

PUBLICATIONS

Faye et al.; "Molecular Evolution of Zika Virus during its Emergence in the 20th Century"; PLOS—Neglected Tropical Diseases, vol. 8, No. 1, Jan. 9, 2014, p. e2636, the entire article.

Cox et al.; Predicting Zika virus structural biology: Challenges and opportunities for intervention; Antiviral Chemistry and Chemotherapy, vol. 24, No. 3-4, Aug. 1, 2016, pp. 118-126.

Shan et al.; "Zika Virus: Diagnosis, Therapeutics, and Vaccine"; ACS—Infectious Diseases, vol. 2, No. 3, Mar. 11, 2016, pp. 170-172.

Martins et al.; "Considerations for the development of Zika virus vaccines"; Vaccine, vol. 34, No. 33, Jun. 16, 2016 pp. 3711-3712.

*Primary Examiner* — Barry A Chestnut
(74) *Attorney, Agent, or Firm* — W&C IP

(57) ABSTRACT

The present invention relates to vaccine compositions comprising an attenuated mutant Zika virus. The inventors have introduced mutations at very specific positions that abrogate the N-glycosylation site on the E protein of the epidemic strain which will prevent the generation of auto-antibodies responsible for Guillain-Barre syndrome. The inventors have also produced additional mutations of the virus that result to a dramatic reduction of the cytopathic effects without affecting the capacity to produce high titers of virus. In particular, the present invention relates to an attenuated mutant Zika virus comprising a protein E of the epidemic strain wherein at least one amino acid residue at position 152, 156 or 158 is mutated.

15 Claims, 4 Drawing Sheets

Specification includes a Sequence Listing.

Figure 1

ZIKV clones

SEQUENCE LISTING

<160> NUMBER OF SEQ ID NOS: 7

<210> SEQ ID NO 1
<211> LENGTH: 504
<212> TYPE: PRT
<213> ORGANISM: Artificial Sequence
<220> FEATURE:
<223> OTHER INFORMATION: Synthetic E glycoprotein from ZIKV strain BeH
     819015 (Genbank access #KU365778.1)

<400> SEQUENCE: 1

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

```
Val Met Ala Gln Asp Lys Pro Thr Val Asp Ile Glu Leu Val Thr Thr
             35                  40                  45
Thr Val Ser Asn Met Ala Glu Val Arg Ser Tyr Cys Tyr Glu Ala Ser
 50                  55                  60
Ile Ser Asp Met Ala Ser Asp Ser Arg Cys Pro Thr Gln Gly Glu Ala
 65                  70                  75                  80
Tyr Leu Asp Lys Gln Ser Asp Thr Gln Tyr Val Cys Lys Arg Thr Leu
                 85                  90                  95
Val Asp Arg Gly Trp Gly Asn Gly Cys Gly Leu Phe Gly Lys Gly Ser
                100                 105                 110
Leu Val Thr Cys Ala Lys Phe Ala Cys Ser Lys Lys Met Thr Gly Lys
            115                 120                 125
Ser Ile Gln Pro Glu Asn Leu Glu Tyr Arg Ile Met Leu Ser Val His
        130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
                195                 200                 205
Lys His Trp Leu Val His Lys Glu Trp Phe His Asp Ile Pro Leu Pro
            210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
        290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460
Gln Ile Leu Ile Gly Thr Leu Leu Met Trp Leu Gly Leu Asn Thr Lys
465                 470                 475                 480
Asn Gly Ser Ile Ser Leu Met Cys Leu Ala Leu Gly Gly Val Leu Ile
                485                 490                 495
Phe Leu Ser Thr Ala Val Ser Ala
            500

<210> SEQ ID NO 2
<211> LENGTH: 504
<212> TYPE: PRT
<213> ORGANISM: Artificial Sequence
<220> FEATURE:
<223> OTHER INFORMATION: Synthetic E sequences of mutant [E-I152T,
      E-T156I, E-H158Y] of ZIKVBR15-MC

<400> SEQUENCE: 2

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
                20                  25                  30
Val Met Ala Gln Asp Lys Pro Thr Val Asp Ile Glu Leu Val Thr Thr
            35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Thr Val Asn Asp Ile Gly Tyr Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
```

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 3
<211> LENGTH: 3423
<212> TYPE: PRT
<213> ORGANISM: Artificial Sequence
<220> FEATURE:
<223> OTHER INFORMATION: Synthetic Polyprotein sequence of chimeric
      ZIKVBR15-MC mutant [E-I152T, E-T156I, E-H158Y ] (3,423 aa)

<400> SEQUENCE: 3

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
```

-continued

```
            145                 150                 155                 160
        Met Asp Leu Gly His Met Cys Asp Ala Thr Met Ser Tyr Glu Cys Pro
                        165                 170                 175
        Met Leu Asp Glu Gly Val Glu Pro Asp Val Asp Cys Trp Cys Asn
                        180                 185                 190
        Thr Thr Ser Thr Trp Val Val Tyr Gly Thr Cys His His Lys Lys Gly
                        195                 200                 205
        Glu Ala Arg Arg Ser Arg Arg Ala Val Thr Leu Pro Ser His Ser Thr
                        210                 215                 220
        Arg Lys Leu Gln Thr Arg Ser Gln Thr Trp Leu Glu Ser Arg Glu Tyr
        225                 230                 235                 240
        Thr Lys His Leu Ile Arg Val Glu Asn Trp Ile Phe Arg Asn Pro Gly
                        245                 250                 255
        Phe Ala Leu Ala Ala Ala Ala Ile Ala Trp Leu Leu Gly Ser Ser Thr
                        260                 265                 270
        Ser Gln Lys Val Ile Tyr Leu Val Met Ile Leu Leu Ile Ala Pro Ala
                        275                 280                 285
        Tyr Ser Ile Arg Cys Ile Gly Val Ser Asn Arg Asp Phe Val Glu Gly
                        290                 295                 300
        Met Ser Gly Gly Thr Trp Val Asp Val Val Leu Glu His Gly Gly Cys
        305                 310                 315                 320
        Val Thr Val Met Ala Gln Asp Lys Pro Thr Val Asp Ile Glu Leu Val
                        325                 330                 335
        Thr Thr Thr Val Ser Asn Met Ala Glu Val Arg Ser Tyr Cys Tyr Glu
                        340                 345                 350
        Ala Ser Ile Ser Asp Met Ala Ser Asp Ser Arg Cys Pro Thr Gln Gly
                        355                 360                 365
        Glu Ala Tyr Leu Asp Lys Gln Ser Asp Thr Gln Tyr Val Cys Lys Arg
                        370                 375                 380
        Thr Leu Val Asp Arg Gly Trp Gly Asn Gly Cys Gly Leu Phe Gly Lys
        385                 390                 395                 400
        Gly Ser Leu Val Thr Cys Ala Lys Phe Ala Cys Ser Lys Lys Met Thr
                        405                 410                 415
        Gly Lys Ser Ile Gln Pro Glu Asn Leu Glu Tyr Arg Ile Met Leu Ser
                        420                 425                 430
        Val His Gly Ser Gln His Ser Gly Met Thr Val Asn Asp Ile Gly Tyr
                        435                 440                 445
        Glu Thr Asp Glu Asn Arg Ala Lys Val Glu Ile Thr Pro Asn Ser Pro
                        450                 455                 460
        Arg Ala Glu Ala Thr Leu Gly Gly Phe Gly Ser Leu Gly Leu Asp Cys
        465                 470                 475                 480
        Glu Pro Arg Thr Gly Leu Asp Phe Ser Asp Leu Tyr Tyr Leu Thr Met
                        485                 490                 495
        Asn Asn Lys His Trp Leu Val His Lys Glu Trp Phe His Asp Ile Pro
                        500                 505                 510
        Leu Pro Trp His Ala Gly Ala Asp Thr Gly Thr Pro His Trp Asn Asn
                        515                 520                 525
        Lys Glu Ala Leu Val Glu Phe Lys Asp Ala His Ala Lys Arg Gln Thr
                        530                 535                 540
        Val Val Val Leu Gly Ser Gln Glu Gly Ala Val His Thr Ala Leu Ala
        545                 550                 555                 560
        Gly Ala Leu Glu Ala Glu Met Asp Gly Ala Lys Gly Arg Leu Ser Ser
                        565                 570                 575
```

-continued

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
        690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
        770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
        850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

```
Gly Tyr Trp Ile Glu Ser Glu Lys  Asn Asp Thr Trp Arg  Leu Lys Arg
        995              1000                1005

Ala His  Leu Ile Glu Met Lys  Thr Cys Glu Trp Pro  Lys Ser His
1010              1015                 1020

Thr Leu  Trp Thr Asp Gly Ile  Glu Glu Ser Asp Leu  Ile Ile Pro
1025              1030                 1035

Lys Ser  Leu Ala Gly Pro Leu  Ser His His Asn Thr  Arg Glu Gly
1040              1045                 1050

Tyr Arg  Thr Gln Met Lys Gly  Pro Trp His Ser Glu  Glu Leu Glu
1055              1060                 1065

Ile Arg  Phe Glu Glu Cys Pro  Gly Thr Lys Val His  Val Glu Glu
1070              1075                 1080

Thr Cys  Gly Thr Arg Gly Pro  Ser Leu Arg Ser Thr  Thr Ala Ser
1085              1090                 1095

Gly Arg  Val Ile Glu Glu Trp  Cys Cys Arg Glu Cys  Thr Met Pro
1100              1105                 1110

Pro Leu  Ser Phe Arg Ala Lys  Asp Gly Cys Trp Tyr  Gly Met Glu
1115              1120                 1125

Ile Arg  Pro Arg Lys Glu Pro  Glu Ser Asn Leu Val  Arg Ser Met
1130              1135                 1140

Val Thr  Ala Gly Ser Thr Asp  His Met Asp His Phe  Ser Leu Gly
1145              1150                 1155

Val Leu  Val Ile Leu Leu Met  Val Gln Glu Gly Leu  Lys Lys Arg
1160              1165                 1170

Met Thr  Thr Lys Ile Ile Ile  Ser Thr Ser Met Ala  Val Leu Val
1175              1180                 1185

Ala Met  Ile Leu Gly Gly Phe  Ser Met Ser Asp Leu  Ala Lys Leu
1190              1195                 1200

Ala Ile  Leu Met Gly Ala Thr  Phe Ala Glu Met Asn  Thr Gly Gly
1205              1210                 1215

Asp Val  Ala His Leu Ala Leu  Ile Ala Ala Phe Lys  Val Arg Pro
1220              1225                 1230

Ala Leu  Leu Val Ser Phe Ile  Phe Arg Ala Asn Trp  Thr Pro Arg
1235              1240                 1245

Glu Ser  Met Leu Leu Ala Leu  Ala Ser Cys Leu Leu  Gln Thr Ala
1250              1255                 1260

Ile Ser  Ala Leu Glu Gly Asp  Leu Met Val Leu Ile  Asn Gly Phe
1265              1270                 1275

Ala Leu  Ala Trp Leu Ala Ile  Arg Ala Met Val Val  Pro Arg Thr
1280              1285                 1290

Asp Asn  Ile Thr Leu Ala Ile  Leu Ala Ala Leu Thr  Pro Leu Ala
1295              1300                 1305

Arg Gly  Thr Leu Leu Val Ala  Trp Arg Ala Gly Leu  Ala Thr Cys
1310              1315                 1320

Gly Gly  Phe Met Leu Leu Ser  Leu Lys Gly Lys Gly  Ser Val Lys
1325              1330                 1335

Lys Asn  Leu Pro Phe Val Met  Ala Leu Gly Leu Thr  Ala Val Arg
1340              1345                 1350

Leu Val  Asp Pro Ile Asn Val  Val Gly Leu Leu Leu  Leu Thr Arg
1355              1360                 1365

Ser Gly  Lys Arg Ser Trp Pro  Pro Ser Glu Val Leu  Thr Ala Val
1370              1375                 1380

Gly Leu  Ile Cys Ala Leu Ala  Gly Gly Phe Ala Lys  Ala Asp Ile
```

-continued

```
            1385                1390                1395
Glu Met Ala Gly Pro Met Ala Val Gly Leu Leu Ile Val Ser
        1400                1405                1410
Tyr Val Val Ser Gly Lys Ser Val Asp Met Tyr Ile Glu Arg Ala
        1415                1420                1425
Gly Asp Ile Thr Trp Glu Lys Asp Ala Glu Val Thr Gly Asn Ser
        1430                1435                1440
Pro Arg Leu Asp Val Ala Leu Asp Glu Ser Gly Asp Phe Ser Leu
        1445                1450                1455
Val Glu Asp Asp Gly Pro Pro Met Arg Glu Ile Ile Leu Lys Val
        1460                1465                1470
Val Leu Met Thr Ile Cys Gly Met Asn Pro Ile Ala Ile Pro Phe
        1475                1480                1485
Ala Ala Gly Ala Trp Tyr Val Tyr Val Lys Thr Gly Lys Arg Ser
        1490                1495                1500
Gly Ala Leu Trp Asp Val Pro Ala Pro Lys Glu Val Lys Lys Gly
        1505                1510                1515
Glu Thr Thr Asp Gly Val Tyr Arg Val Met Thr Arg Arg Leu Leu
        1520                1525                1530
Gly Ser Thr Gln Val Gly Val Gly Val Met Gln Glu Gly Val Phe
        1535                1540                1545
His Thr Met Trp His Val Thr Lys Gly Ser Ala Leu Arg Ser Gly
        1550                1555                1560
Glu Gly Arg Leu Asp Pro Tyr Trp Gly Asp Val Lys Gln Asp Leu
        1565                1570                1575
Val Ser Tyr Cys Gly Pro Trp Lys Leu Asp Ala Ala Trp Asp Gly
        1580                1585                1590
His Ser Glu Val Gln Leu Leu Ala Val Pro Pro Gly Glu Arg Ala
        1595                1600                1605
Arg Asn Ile Gln Thr Leu Pro Gly Ile Phe Lys Thr Lys Asp Gly
        1610                1615                1620
Asp Ile Gly Ala Val Ala Leu Asp Tyr Pro Ala Gly Thr Ser Gly
        1625                1630                1635
Ser Pro Ile Leu Asp Lys Cys Gly Arg Val Ile Gly Leu Tyr Gly
        1640                1645                1650
Asn Gly Val Val Ile Lys Asn Gly Ser Tyr Val Ser Ala Ile Thr
        1655                1660                1665
Gln Gly Arg Arg Glu Glu Glu Thr Pro Val Glu Cys Phe Glu Pro
        1670                1675                1680
Ser Met Leu Lys Lys Lys Gln Leu Thr Val Leu Asp Leu His Pro
        1685                1690                1695
Gly Ala Gly Lys Thr Arg Arg Val Leu Pro Glu Ile Val Arg Glu
        1700                1705                1710
Ala Ile Lys Thr Arg Leu Arg Thr Val Ile Leu Ala Pro Thr Arg
        1715                1720                1725
Val Val Ala Ala Glu Met Glu Glu Ala Leu Arg Gly Leu Pro Val
        1730                1735                1740
Arg Tyr Met Thr Thr Ala Val Asn Val Thr His Ser Gly Thr Glu
        1745                1750                1755
Ile Val Asp Leu Met Cys His Ala Thr Phe Thr Ser Arg Leu Leu
        1760                1765                1770
Gln Pro Ile Arg Val Pro Asn Tyr Asn Leu Tyr Ile Met Asp Glu
        1775                1780                1785
```

```
Ala His Phe Thr Asp Pro Ser Ser Ile Ala Ala Arg Gly Tyr Ile
    1790            1795                1800

Ser Thr Arg Val Glu Met Gly Glu Ala Ala Ile Phe Met Thr
    1805            1810                1815

Ala Thr Pro Pro Gly Thr Arg Asp Ala Phe Pro Asp Ser Asn Ser
    1820            1825                1830

Pro Ile Met Asp Thr Glu Val Glu Val Pro Glu Arg Ala Trp Ser
    1835            1840                1845

Ser Gly Phe Asp Trp Val Thr Asp His Ser Gly Lys Thr Val Trp
    1850            1855                1860

Phe Val Pro Ser Val Arg Asn Gly Asn Glu Ile Ala Ala Cys Leu
    1865            1870                1875

Thr Lys Ala Gly Lys Arg Val Ile Gln Leu Ser Arg Lys Thr Phe
    1880            1885                1890

Glu Thr Glu Phe Gln Lys Thr Lys His Gln Glu Trp Asp Phe Val
    1895            1900                1905

Val Thr Thr Asp Ile Ser Glu Met Gly Ala Asn Phe Lys Ala Asp
    1910            1915                1920

Arg Val Ile Asp Ser Arg Arg Cys Leu Lys Pro Val Ile Leu Asp
    1925            1930                1935

Gly Glu Arg Val Ile Leu Ala Gly Pro Met Pro Val Thr His Ala
    1940            1945                1950

Ser Ala Ala Gln Arg Arg Gly Arg Ile Gly Arg Asn Pro Asn Lys
    1955            1960                1965

Pro Gly Asp Glu Tyr Leu Tyr Gly Gly Gly Cys Ala Glu Thr Asp
    1970            1975                1980

Glu Asp His Ala His Trp Leu Glu Ala Arg Met Leu Leu Asp Asn
    1985            1990                1995

Ile Tyr Leu Gln Asp Gly Leu Ile Ala Ser Leu Tyr Arg Pro Glu
    2000            2005                2010

Ala Asp Lys Val Ala Ala Ile Glu Gly Glu Phe Lys Leu Arg Thr
    2015            2020                2025

Glu Gln Arg Lys Thr Phe Val Glu Leu Met Lys Arg Gly Asp Leu
    2030            2035                2040

Pro Val Trp Leu Ala Tyr Gln Val Ala Ser Ala Gly Ile Thr Tyr
    2045            2050                2055

Thr Asp Arg Arg Trp Cys Phe Asp Gly Thr Thr Asn Asn Thr Ile
    2060            2065                2070

Met Glu Asp Ser Val Pro Ala Glu Val Trp Thr Arg His Gly Glu
    2075            2080                2085

Lys Arg Val Leu Lys Pro Arg Trp Met Asp Ala Arg Val Cys Ser
    2090            2095                2100

Asp His Ala Ala Leu Lys Ser Phe Lys Glu Phe Ala Ala Gly Lys
    2105            2110                2115

Arg Gly Ala Ala Phe Gly Val Met Glu Ala Leu Gly Thr Leu Pro
    2120            2125                2130

Gly His Met Thr Glu Arg Phe Gln Glu Ala Ile Asp Asn Leu Ala
    2135            2140                2145

Val Leu Met Arg Ala Glu Thr Gly Ser Arg Pro Tyr Lys Ala Ala
    2150            2155                2160

Ala Ala Gln Leu Pro Glu Thr Leu Glu Thr Ile Met Leu Leu Gly
    2165            2170                2175
```

```
Leu Leu Gly Thr Val Ser Leu Gly Ile Phe Phe Val Leu Met Arg
    2180              2185              2190

Asn Lys Gly Ile Gly Lys Met Gly Phe Gly Met Val Thr Leu Gly
    2195              2200              2205

Ala Ser Ala Trp Leu Met Trp Leu Ser Glu Ile Glu Pro Ala Arg
    2210              2215              2220

Ile Ala Cys Val Leu Ile Val Val Phe Leu Leu Leu Val Val Leu
    2225              2230              2235

Ile Pro Glu Pro Glu Lys Gln Arg Ser Pro Gln Asp Asn Gln Met
    2240              2245              2250

Ala Ile Ile Ile Met Val Ala Val Gly Leu Leu Gly Leu Ile Thr
    2255              2260              2265

Ala Asn Glu Leu Gly Trp Leu Glu Arg Thr Lys Ser Asp Leu Ser
    2270              2275              2280

His Leu Met Gly Arg Arg Glu Glu Gly Ala Thr Ile Gly Phe Ser
    2285              2290              2295

Met Asp Ile Asp Leu Arg Pro Ala Ser Ala Trp Ala Ile Tyr Ala
    2300              2305              2310

Ala Leu Thr Thr Phe Ile Thr Pro Ala Val Gln His Ala Val Thr
    2315              2320              2325

Thr Ser Tyr Asn Asn Tyr Ser Leu Met Ala Met Ala Thr Gln Ala
    2330              2335              2340

Gly Val Leu Phe Gly Met Gly Lys Gly Met Pro Phe Tyr Ala Trp
    2345              2350              2355

Asp Phe Gly Val Pro Leu Leu Met Ile Gly Cys Tyr Ser Gln Leu
    2360              2365              2370

Thr Pro Leu Thr Leu Ile Val Ala Ile Ile Leu Leu Val Ala His
    2375              2380              2385

Tyr Met Tyr Leu Ile Pro Gly Leu Gln Ala Ala Ala Ala Arg Ala
    2390              2395              2400

Ala Gln Lys Arg Thr Ala Ala Gly Ile Met Lys Asn Pro Val Val
    2405              2410              2415

Asp Gly Ile Val Val Thr Asp Ile Asp Thr Met Thr Ile Asp Pro
    2420              2425              2430

Gln Val Glu Lys Lys Met Gly Gln Val Leu Leu Ile Ala Val Ala
    2435              2440              2445

Val Ser Ser Ala Ile Leu Ser Arg Thr Ala Trp Gly Trp Gly Glu
    2450              2455              2460

Ala Gly Ala Leu Ile Thr Ala Ala Thr Ser Thr Leu Trp Glu Gly
    2465              2470              2475

Ser Pro Asn Lys Tyr Trp Asn Ser Ser Thr Ala Thr Ser Leu Cys
    2480              2485              2490

Asn Ile Phe Arg Gly Ser Tyr Leu Ala Gly Ala Ser Leu Ile Tyr
    2495              2500              2505

Thr Val Thr Arg Asn Ala Gly Leu Val Lys Arg Arg Gly Gly Gly
    2510              2515              2520

Thr Gly Glu Thr Leu Gly Glu Lys Trp Lys Ala Arg Leu Asn Gln
    2525              2530              2535

Met Ser Ala Leu Glu Phe Tyr Ser Tyr Lys Lys Ser Gly Ile Thr
    2540              2545              2550

Glu Val Cys Arg Glu Glu Ala Arg Arg Ala Leu Lys Asp Gly Val
    2555              2560              2565

Ala Thr Gly Gly His Ala Val Ser Arg Gly Ser Ala Lys Leu Arg
```

```
                2570                2575                2580
Trp Leu Val Glu Arg Gly Tyr Leu Gln Pro Tyr Gly Lys Val Ile
    2585                2590                2595
Asp Leu Gly Cys Gly Arg Gly Gly Trp Ser Tyr Tyr Ala Ala Thr
    2600                2605                2610
Ile Arg Lys Val Gln Glu Val Lys Gly Tyr Thr Lys Gly Gly Pro
    2615                2620                2625
Gly His Glu Glu Pro Val Leu Val Gln Ser Tyr Gly Trp Asn Ile
    2630                2635                2640
Val Arg Leu Lys Ser Gly Val Asp Val Phe His Met Ala Ala Glu
    2645                2650                2655
Pro Cys Asp Thr Leu Leu Cys Asp Ile Gly Glu Ser Ser Ser Ser
    2660                2665                2670
Pro Glu Val Glu Glu Ala Arg Thr Leu Arg Val Leu Ser Met Val
    2675                2680                2685
Gly Asp Trp Leu Glu Lys Arg Pro Gly Ala Phe Cys Ile Lys Val
    2690                2695                2700
Leu Cys Pro Tyr Thr Ser Thr Met Met Glu Thr Leu Glu Arg Leu
    2705                2710                2715
Gln Arg Arg Tyr Gly Gly Gly Leu Val Arg Val Pro Leu Ser Arg
    2720                2725                2730
Asn Ser Thr His Glu Met Tyr Trp Val Ser Gly Ala Lys Ser Asn
    2735                2740                2745
Thr Ile Lys Ser Val Ser Thr Thr Ser Gln Leu Leu Leu Gly Arg
    2750                2755                2760
Met Asp Gly Pro Arg Arg Pro Val Lys Tyr Glu Glu Asp Val Asn
    2765                2770                2775
Leu Gly Ser Gly Thr Arg Ala Val Val Ser Cys Ala Glu Ala Pro
    2780                2785                2790
Asn Met Lys Ile Ile Gly Asn Arg Ile Glu Arg Ile Arg Ser Glu
    2795                2800                2805
His Ala Glu Thr Trp Phe Phe Asp Glu Asn His Pro Tyr Arg Thr
    2810                2815                2820
Trp Ala Tyr His Gly Ser Tyr Glu Ala Pro Thr Gln Gly Ser Ala
    2825                2830                2835
Ser Ser Leu Ile Asn Gly Val Val Arg Leu Leu Ser Lys Pro Trp
    2840                2845                2850
Asp Val Val Thr Gly Val Thr Gly Ile Ala Met Thr Asp Thr Thr
    2855                2860                2865
Pro Tyr Gly Gln Gln Arg Val Phe Lys Glu Lys Val Asp Thr Arg
    2870                2875                2880
Val Pro Asp Pro Gln Glu Gly Thr Arg Gln Val Met Ser Met Val
    2885                2890                2895
Ser Ser Trp Leu Trp Lys Glu Leu Gly Lys His Lys Arg Pro Arg
    2900                2905                2910
Val Cys Thr Lys Glu Glu Phe Ile Asn Lys Val Arg Ser Asn Ala
    2915                2920                2925
Ala Leu Gly Ala Ile Phe Glu Glu Glu Lys Glu Trp Lys Thr Ala
    2930                2935                2940
Val Glu Ala Val Asn Asp Pro Arg Phe Trp Ala Leu Val Asp Lys
    2945                2950                2955
Glu Arg Glu His His Leu Arg Gly Glu Cys Gln Ser Cys Val Tyr
    2960                2965                2970
```

-continued

Asn Met Met Gly Lys Arg Glu Lys Lys Gln Gly Glu Phe Gly Lys
2975            2980            2985

Ala Lys Gly Ser Arg Ala Ile Trp Tyr Met Trp Leu Gly Ala Arg
2990            2995            3000

Phe Leu Glu Phe Glu Ala Leu Gly Phe Leu Asn Glu Asp His Trp
3005            3010            3015

Met Gly Arg Glu Asn Ser Gly Gly Val Gly Leu Gly Leu
3020            3025            3030

Gln Arg Leu Gly Tyr Val Leu Glu Glu Met Ser Arg Ile Pro Gly
3035            3040            3045

Gly Arg Met Tyr Ala Asp Asp Thr Ala Gly Trp Asp Thr Arg Ile
3050            3055            3060

Ser Arg Phe Asp Leu Glu Asn Glu Ala Leu Ile Thr Asn Gln Met
3065            3070            3075

Glu Lys Gly His Arg Ala Leu Ala Leu Ala Ile Ile Lys Tyr Thr
3080            3085            3090

Tyr Gln Asn Lys Val Val Lys Val Leu Arg Pro Ala Glu Lys Gly
3095            3100            3105

Lys Thr Val Met Asp Ile Ile Ser Arg Gln Asp Gln Arg Gly Ser
3110            3115            3120

Gly Gln Val Val Thr Tyr Ala Leu Asn Thr Phe Thr Asn Leu Val
3125            3130            3135

Val Gln Leu Ile Arg Asn Met Glu Ala Glu Glu Val Leu Glu Met
3140            3145            3150

Gln Asp Leu Trp Leu Leu Arg Arg Ser Glu Lys Val Thr Asn Trp
3155            3160            3165

Leu Gln Ser Asn Gly Trp Asp Arg Leu Lys Arg Met Ala Val Ser
3170            3175            3180

Gly Asp Asp Cys Val Val Lys Pro Ile Asp Asp Arg Phe Ala His
3185            3190            3195

Ala Leu Arg Phe Leu Asn Asp Met Gly Lys Val Arg Lys Asp Thr
3200            3205            3210

Gln Glu Trp Lys Pro Ser Thr Gly Trp Asp Asn Trp Glu Glu Val
3215            3220            3225

Pro Phe Cys Ser His His Phe Asn Lys Leu His Leu Lys Asp Gly
3230            3235            3240

Arg Ser Ile Val Val Pro Cys Arg His Gln Asp Glu Leu Ile Gly
3245            3250            3255

Arg Ala Arg Val Ser Pro Gly Ala Gly Trp Ser Ile Arg Glu Thr
3260            3265            3270

Ala Cys Leu Ala Lys Ser Tyr Ala Gln Met Trp Gln Leu Leu Tyr
3275            3280            3285

Phe His Arg Arg Asp Leu Arg Leu Met Ala Asn Ala Ile Cys Ser
3290            3295            3300

Ser Val Pro Val Asp Trp Val Pro Thr Gly Arg Thr Thr Trp Ser
3305            3310            3315

Ile His Gly Lys Gly Glu Trp Met Thr Thr Glu Asp Met Leu Val
3320            3325            3330

Val Trp Asn Arg Val Trp Ile Glu Glu Asn Asp His Met Glu Asp
3335            3340            3345

Lys Thr Pro Val Thr Lys Trp Thr Asp Ile Pro Tyr Leu Gly Lys
3350            3355            3360

```
Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
        3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420

<210> SEQ ID NO 4
<211> LENGTH: 10807
<212> TYPE: DNA
<213> ORGANISM: Artificial Sequence
<220> FEATURE:
<223> OTHER INFORMATION: Synthetic Genomic sequence of chimeric
      ZIKVBR15-MC mutant [E-I152T, E-T156I, E-H158Y ] (10,807 nt)

<400> SEQUENCE: 4
agttgttgat ctgtgtgagt cagactgcga cagttcgagt ctgaagcgag agctaacaac      60
agtatcaaca ggtttaattt ggatttggaa acgagagttt ctggtcatga aaacccaaa     120 aaagaaatcc ggaggattcc ggattgtcaa tatgctaaaa cgcggagtag cccgtgtgag     180 ccccttggg ggcttgaaga ggctgccagc cggacttctg ctgggtcatg ggcccatcag     240
gatggtcttg gcgattctag ccttttgag attcacggca atcaagccat cactgggtct     300
catcaataga tggggttcag ttgggaaaaa agaggctatg gaaataataa agaagttcaa     360
gaaagatctg gctgccatgc tgagaataat caatgctagg aaggagaaga gagacgagg     420 cgcagatact agtgtcggaa ttgttggcct cctgctgacc acagctatgg cagcggaggt     480
cactagacgt gggagtgcat actatatgta cttggacaga aacgatgctg gggaggccat     540
atcttttcca accacattgg ggatgaataa gtgttatata cagatcatgg atcttggaca     600
catgtgtgat gccaccatga gctatgaatg ccctatgctg gatgaggggg tgaaccaga     660 tgacgtcgat tgttggtgca acacgacgtc aacttgggtt gtgtacggaa cctgccatca     720 caaaaaggt gaagcacgga gatctagaag agctgtgacg ctcccctccc attccactag     780
gaagctgcaa acgcggtcgc aaacctggtt ggaatcaaga gaatacacaa agcacttgat     840
tagagtcgaa aattggatat tcaggaaccc tggcttcgcg ttagcagcag ctgccatcgc     900
ttggcttttg ggaagctcaa cgagccaaaa agtcatatac ttggtcatga tactgctgat     960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca acagtcagca acatggcgga    1140
ggtacgatcg tactgctatg aggcatcaat atcagacatg gcttcggaca gccgctgccc    1200
aacacaaggt gaagcctacc ttgacaagca atcagacact caatatgtct gcaaaagaac    1260
gttagtggac agaggctggg gaaatggatg tggactttt ggcaaaggga gcctggtgac    1320
atgcgctaag tttgcatgct ccaagaaaat gaccgggaag agcatccagc cagagaatct    1380
ggagtaccgg ataatgctgt cagttcatgg ctcccagcac agtgggatga ctgtcaatga    1440
tataggatat gaaactgatg agaatagagc gaaagttgag ataacgccca attcaccaag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg gcacgctggg gcagacaccg gaactccaca    1680
```

```
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg aaggctgtc ctctggccac ttgaaatgtc gcctgaaaat     1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgaccccagt    2040
tgggaggttg ataaccgcta accccgtaat cactgaaagc actgagaact ctaagatgat    2100
gctggaactt gatccaccat ttgggactc ttacattgtc ataggagtcg gggagaagaa     2160
gatcacccac cactggcaca ggagtggcag caccattgga aaagcatttg aggccactgt    2220
gagaggcgcc aagagaatgg cagtcctggg ggacacagcc tggactttg atcagttgg      2280 aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggccttag ggggggtgtt    2460
gatcttctta tccacagccg tctctgctga tgtggggtgc tcggtggact tctcaaagaa    2520
ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa acatcatgt ggagatcagt     2700 agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gtacttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa aacatgtgaa tggccaaagt cccacacatt    3180
gtggacagat ggaatagaag agagtgatct gatcataccc aagtctttag ctgggccact    3240
cagccatcac aataccagag agggctacag gaccccaaatg aaagggccat ggcacagtga   3300
agagcttgaa attcggtttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg ctgttggta    3480 tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacacccggt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcgggg    4080
```

```
gtttatgctc ctctctctga agggaaaagg cagtgtgaag aagaacttac catttgtcat      4140
ggccctggga ctaaccgctg tgaggctggt cgacccatc aacgtggtgg gactgctgtt       4200
actcacaagg agtgggaagc ggagctggcc ccctagcgaa gtactcacag ctgttggcct      4260
gatatgcgca ttggctggag ggttcgccaa ggcagatata gagatggctg ggcccatggc      4320
cgcggtcggt ctgctaattg tcagttacgt ggtctcagga aagagtgtgg acatgtacat      4380
tgaaagagca ggtgacatca catgggaaaa agatgcggga gtcactggaa acagtccccg      4440
gctcgatgtg gcgctagatg agagtggtga tttctccctg gtggaggatg acggtccccc      4500
catgagagag atcatactca aggtggtcct gatgaccatc tgtggcatga atccaatagc      4560
catacccttt gcagctggag cgtggtacgt atacgtgaag actggaaaaa ggagtggtgc      4620
tctatgggat gtgcctgctc ccaaggaagt aaaaaagggg gagaccacag atggagtgta      4680
cagagtaatg actcgtagac tgctaggttc aacacaagtt ggagtgggag ttatgcaaga      4740
gggggtcttt cacactatgt ggcacgtcac aaaaggatcc gcgctgagaa gcggtgaagg      4800
gagacttgat ccatactggg gagatgtcaa gcaggatctg gtgtcatact gtggtccatg      4860
gaagctagat gccgcctggg acgggcacag cgaggtgcag ctcttggccg tgccccccgg      4920
agagagagcg aggaacatcc agactctgcc cggaatattt aagacaaagg atggggacat      4980
tggagcggtt gcgctggatt acccagcagg aacttcagga tctccaatcc tagacaagtg      5040
tgggagagtg ataggacttt atggcaatgg ggtcgtgatc aaaaatggga gttatgttag      5100
tgccatcacc caagggagga gggaagaaga gactcctgtt gagtgcttcg agccctcgat      5160
gctgaagaag aagcagctaa ctgtcttaga cttgcatcct ggagctggga aaaccaggag      5220
agttcttcct gaaatagtcc gtgaagccat aaaaacaaga ctccgtactg tgatcttagc      5280
tccaaccagg gttgtcgctg ctgaaatgga ggaggccctt agagggcttc cagtgcgtta      5340
tatgacaaca gcagtcaatg tcacccactc tggaacagaa atcgtcgact taatgtgcca      5400
tgccaccttc acttcacgtc tactacagcc aatcagagtc cccaactata atctgtatat      5460
tatggatgag gcccacttca cagatccctc aagtatagca gcaagaggat acatttcaac      5520
aagggttgag atgggcgagg cggctgccat cttcatgacc gccacgccac caggaacccg      5580
tgacgcattt ccggactcca actcaccaat tatggacacc gaagtggaag tcccagagag      5640
agcctggagc tcaggctttg attgggtgac ggatcattct ggaaaaacag tttggtttgt      5700
tccaagcgtg aggaacggca atgagatcgc agcttgtctg acaaaggctg aaaacgggt       5760 catacagctc agcagaaaga cttttgagac agagttccag aaaacaaaac atcaagagtg      5820 ggacttgtc gtgacaactg acatttcaga gatgggcgcc aactttaaag ctgaccgtgt       5880
catagattcc aggagatgcc taaagccggt catacttgat ggcagagag tcattctggc       5940 tggacccatg cctgtcacac atgccagcgc tgcccagagg agggggcgca taggcaggaa      6000
tcccaacaaa cctggagatg agtatctgta tggaggtggg tgcgcagaga ctgacgaaga      6060
ccatgcacac tggcttgaag caagaatgct ccttgacaat atttacctcc aagatggcct      6120
catagcctcg ctctatcgac ctgaggccga caaagtagca gccattgagg gagagttcaa      6180
gcttaggacg gagcaaagga agacctttgt ggaactcatg aaaagaggag atcttcctgt      6240
ttggctggcc tatcaggttg catctgccgg aataacctac acagatagaa gatggtgctt      6300
tgatggcacg accaacaaca ccataatgga agatagtgtg ccggcagagg tgtggaccag      6360
acacggagag aaaagagtgc tcaaaccgag gtggatggac gccagagttt gttcagatca      6420
```

```
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg agaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attccccag ccgtccaaca    7080 tgcagtgacc acttcataca caactactc cttaatggcg atggccacgc aagctggagt    7140
gttgtttggt atgggcaaag gatgccatt ctacgcatgg gactttggag tcccgctgct    7200
aatgataggt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccaagt ggagaaaaag atgggacagg tgctactcat    7440
agcagtagcc gtctccagcg ccatactgtc gcggaccgcc tgggggtggg gggaggctgg    7500
ggccctgatc acagccgcaa cttccacttt gtgggaaggc tctccgaaca agtactggaa    7560
ctcctctaca gccacttcac tgtgtaacat ttttaggggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860 ggtgagcgg ggatacctgc agccctatgg aaaggtcatt gatcttggat gtggcagagg    7920
gggctggagt tactacgccg ccaccatccg caaagttcaa gaagtgaaag atacacaaa    7980 aggaggccct ggtcatgaag aacccgtgtt ggtgcaaagc tatgggtgga acatagtccg    8040
tcttaagagt ggggtggacg tctttcatat ggcggctgag ccgtgtgaca cgctgctgtg    8100
tgacataggt gagtcatcat ctagtcctga agtggaagaa gcacgacgc tcagagtcct    8160 ctccatggtg ggggattggc ttgaaaaaag accaggagcc ttttgtataa aagtgttgtg    8220
cccatacacc agcactatga tggaaaccct ggagcgactg cagcgtaggt atggggagg    8280 actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggctctg cacgcgggc    8460 tgtggtaagc tgcgctgaag ctcccaacat gaagatcatt ggtaaccgca ttgaaaggat    8520
ccgcagtgag cacgcggaaa cgtggttctt tgacgagaac caccatata ggacatgggc    8580 ttaccatgga agctatgagg cccccacaca agggtcagcg tcctctctaa taacggggt    8640 tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760 agaccccaa gaaggcactc gtcaggttat gagcatggtc tcttcctggt tgtggaaaga    8820
```

```
gctaggcaaa cacaaacggc cacgagtctg taccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagttgtg tgtataacat gatgggaaaa agagaaaaga aacaagggga    9060
atttggaaag gccaagggca gccgcgccat ctggtatatg tggctagggg ctagatttct    9120
agagttcgaa gcccttggat tcttgaacga ggatcactgg atgggagag agaactcagg     9180 aggtggtgtt gaagggctgg gattacaaag actcggatat gtcctagaag agatgagtcg    9240
tataccagga ggaaggatgt atgcagatga cactgctggc tgggcacccc gcattagcag    9300
gtttgatctg gagaatgaag ctctaatcac caaccaaatg gagaaagggc acagggcctt    9360
ggcattggcc ataatcaagt acacatacca aacaaagtg gtaaaggtcc ttagaccagc     9420
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gttttgcacat gccctcaggt tcttgaatga    9720
tatgggaaaa gttagaaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc agatgtggca    9960
gctcctttat ttccacagaa gggacctccg actgatggcc aatgccattt gttcatctgt   10020
gccagttgac tgggttccaa ctgggagaac tacctggtca atccatggaa agggagaatg   10080
gatgaccact gaagacatgc ttgtggtgtg aacagagtg tggattgagg agaacgacca    10140 catgaagac aagaccccag ttacgaaatg acagacatt ccctatttgg gaaaagggga     10200
agacttgtgg tgtggatctc tcataggca cagaccgcgc accacctggg ctgagaacat    10260
taaaaacaca gtcaacatgg tgcgcaggat cataggtgat gaagaaaagt acatggacta   10320
cctatccacc caagttcgct acttgggtga agaagggtct acacctggag tgctgtaagc   10380 accaattta gtgttgtcag gcctgctagt cagccacagt ttggggaaag ctgtgcagcc    10440
tgtaaccccc ccaggagaag ctgggaaacc aagctcatag tcaggccgag aacgccatgg   10500
cacggaagaa gccatgctgc ctgtgagccc tcagaggac actgagtcaa aaaccccac     10560 gcgcttggaa gcgcaggatg ggaaaagaag gtggcgacct tccccaccct tcaatctggg   10620
gcctgaactg gagactagct gtgaatctcc agcagggga ctagtggtta gaggagaccc    10680
cccggaaaac gcaaaacagc atattgacgc tgggaaagac cagagactcc atgagtttcc   10740
accacgctgg ccgccaggca cagatcgccg aacagcggcg ccggtgtggg ggaaatccat   10800
ggtttct                                                            10807
```

<210> SEQ ID NO 5
<211> LENGTH: 3423
<212> TYPE: PRT
<213> ORGANISM: Artificial Sequence
<220> FEATURE:
<223> OTHER INFORMATION: Synthetic Polyprotein sequence the chimeric
      ZIKALIVax virus (10,807 nt; 3,423 aa)

<400> SEQUENCE: 5

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
            165                 170                 175

Met Leu Asp Glu Gly Val Glu Pro Asp Asp Val Asp Cys Trp Cys Asn
        180                 185                 190

Thr Thr Ser Thr Trp Val Val Tyr Gly Thr Cys His His Lys Lys Gly
    195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
            245                 250                 255

Phe Ala Leu Ala Ala Ala Ala Ile Ala Trp Leu Leu Gly Ser Ser Thr
        260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
            325                 330                 335

Thr Thr Thr Val Ser Asn Met Ala Glu Val Arg Ser Tyr Cys Tyr Glu
        340                 345                 350

Ala Ser Ile Ser Asp Met Ala Ser Asp Ser Arg Cys Pro Thr Gln Gly
    355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
            405                 410                 415
```

```
Gly Lys Ser Ile Gln Pro Glu Asn Leu Glu Tyr Arg Ile Met Leu Ser
            420                 425                 430

Val His Gly Ser Gln His Ser Gly Met Thr Val Asn Asp Ile Gly Tyr
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Val Phe Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Val Trp Leu Gly Leu Asn
        755                 760                 765

Thr Lys Asn Gly Ser Ile Ser Leu Thr Cys Leu Ala Leu Gly Gly Val
    770                 775                 780

Met Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Ile Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Glu Gly Ile
```

-continued

```
                835                 840                 845
Cys Gly Ile Ser Ser Val Ser Arg Met Glu Asn Ile Met Trp Lys Ser
            850                 855                 860
Val Glu Gly Glu Leu Asn Ala Ile Leu Glu Glu Asn Gly Val Gln Leu
865                 870                 875                 880
Thr Val Val Val Gly Ser Val Lys Asn Pro Met Trp Arg Gly Pro Gln
                885                 890                 895
Arg Leu Pro Val Pro Val Asn Glu Leu Pro His Gly Trp Lys Ala Trp
            900                 905                 910
Gly Lys Ser Tyr Phe Val Arg Ala Ala Lys Thr Asn Asn Ser Phe Val
            915                 920                 925
Val Asp Gly Asp Thr Leu Lys Glu Cys Pro Leu Glu His Arg Ala Trp
            930                 935                 940
Asn Ser Phe Leu Val Glu Asp His Gly Phe Gly Val Phe His Thr Ser
945                 950                 955                 960
Val Trp Leu Lys Val Arg Glu Asp Tyr Ser Leu Glu Cys Asp Pro Ala
                965                 970                 975
Val Ile Gly Thr Ala Val Lys Gly Arg Glu Ala Ala His Ser Asp Leu
            980                 985                 990
Gly Tyr Trp Ile Glu Ser Glu Lys Asn Asp Thr Trp Arg Leu Lys Arg
            995                 1000                1005
Ala His Leu Ile Glu Met Lys Thr Cys Glu Trp Pro Lys Ser His
        1010                1015                1020
Thr Leu Trp Thr Asp Gly Val Glu Glu Ser Asp Leu Ile Ile Pro
        1025                1030                1035
Lys Ser Leu Ala Gly Pro Leu Ser His His Asn Thr Arg Glu Gly
        1040                1045                1050
Tyr Arg Thr Gln Val Lys Gly Pro Trp His Ser Glu Glu Leu Glu
        1055                1060                1065
Ile Arg Phe Glu Glu Cys Pro Gly Thr Lys Val Tyr Val Glu Glu
        1070                1075                1080
Thr Cys Gly Thr Arg Gly Pro Ser Leu Arg Ser Thr Thr Ala Ser
        1085                1090                1095
Gly Arg Val Ile Glu Glu Trp Cys Cys Arg Glu Cys Thr Met Pro
        1100                1105                1110
Pro Leu Ser Phe Arg Ala Lys Asp Gly Cys Trp Tyr Gly Met Glu
        1115                1120                1125
Ile Arg Pro Arg Lys Glu Pro Glu Ser Asn Leu Val Arg Ser Met
        1130                1135                1140
Val Thr Ala Gly Ser Thr Asp His Met Asp His Phe Ser Leu Gly
        1145                1150                1155
Val Leu Val Ile Leu Leu Met Val Gln Glu Gly Leu Lys Lys Arg
        1160                1165                1170
Met Thr Thr Lys Ile Ile Met Ser Thr Ser Met Ala Val Leu Val
        1175                1180                1185
Val Met Ile Leu Gly Gly Phe Ser Met Ser Asp Leu Ala Lys Leu
        1190                1195                1200
Val Ile Leu Met Gly Ala Thr Phe Ala Glu Met Asn Thr Gly Gly
        1205                1210                1215
Asp Val Ala His Leu Ala Leu Val Ala Ala Phe Lys Val Arg Pro
        1220                1225                1230
Ala Leu Leu Val Ser Phe Ile Phe Arg Ala Asn Trp Thr Pro Arg
        1235                1240                1245
```

```
Glu Ser Met Leu Leu Ala Leu Ala Ser Cys Leu Leu Gln Thr Ala
    1250            1255            1260

Ile Ser Ala Leu Glu Gly Asp Leu Met Val Leu Ile Asn Gly Phe
    1265            1270            1275

Ala Leu Ala Trp Leu Ala Ile Arg Ala Met Ala Val Pro Arg Thr
    1280            1285            1290

Asp Asn Ile Ala Leu Pro Ile Leu Ala Ala Leu Thr Pro Leu Ala
    1295            1300            1305

Arg Gly Thr Leu Leu Val Ala Trp Arg Ala Gly Leu Ala Thr Cys
    1310            1315            1320

Gly Gly Ile Met Leu Leu Ser Leu Lys Gly Lys Gly Ser Val Lys
    1325            1330            1335

Lys Asn Leu Pro Phe Val Met Ala Leu Gly Leu Thr Ala Val Arg
    1340            1345            1350

Val Val Asp Pro Ile Asn Val Val Gly Leu Leu Leu Leu Thr Arg
    1355            1360            1365

Ser Gly Lys Arg Ser Trp Pro Pro Ser Glu Val Leu Thr Ala Val
    1370            1375            1380

Gly Leu Ile Cys Ala Leu Ala Gly Gly Phe Ala Lys Ala Asp Ile
    1385            1390            1395

Glu Met Ala Gly Pro Met Ala Ala Val Gly Leu Leu Ile Val Ser
    1400            1405            1410

Tyr Val Val Ser Gly Lys Ser Val Asp Met Tyr Ile Glu Arg Ala
    1415            1420            1425

Gly Asp Ile Thr Trp Glu Lys Asp Ala Glu Val Thr Gly Asn Ser
    1430            1435            1440

Pro Arg Leu Asp Val Ala Leu Asp Glu Ser Gly Asp Phe Ser Leu
    1445            1450            1455

Val Glu Glu Asp Gly Pro Pro Met Arg Glu Ile Ile Leu Lys Val
    1460            1465            1470

Val Leu Met Ala Ile Cys Gly Met Asn Pro Ile Ala Ile Pro Phe
    1475            1480            1485

Ala Ala Gly Ala Trp Tyr Val Tyr Val Lys Thr Gly Lys Arg Ser
    1490            1495            1500

Gly Ala Leu Trp Asp Val Pro Ala Pro Lys Glu Val Lys Lys Gly
    1505            1510            1515

Glu Thr Thr Asp Gly Val Tyr Arg Val Met Thr Arg Arg Leu Leu
    1520            1525            1530

Gly Ser Thr Gln Val Gly Val Gly Val Met Gln Glu Gly Val Phe
    1535            1540            1545

His Thr Met Trp His Val Thr Lys Gly Ala Ala Leu Arg Ser Gly
    1550            1555            1560

Glu Gly Arg Leu Asp Pro Tyr Trp Gly Asp Val Lys Gln Asp Leu
    1565            1570            1575

Val Ser Tyr Cys Gly Pro Trp Lys Leu Asp Ala Ala Trp Asp Gly
    1580            1585            1590

Leu Ser Glu Val Gln Leu Leu Ala Val Pro Pro Gly Glu Arg Ala
    1595            1600            1605

Arg Asn Ile Gln Thr Leu Pro Gly Ile Phe Lys Thr Lys Asp Gly
    1610            1615            1620

Asp Ile Gly Ala Val Ala Leu Asp Tyr Pro Ala Gly Thr Ser Gly
    1625            1630            1635
```

-continued

```
Ser Pro Ile Leu Asp Lys Cys Gly Arg Val Ile Gly Leu Tyr Gly
1640                1645                1650

Asn Gly Val Val Ile Lys Asn Gly Ser Tyr Val Ser Ala Ile Thr
1655                1660                1665

Gln Gly Lys Arg Glu Glu Thr Pro Val Glu Cys Phe Glu Pro
1670                1675                1680

Ser Met Leu Lys Lys Lys Gln Leu Thr Val Leu Asp Leu His Pro
1685                1690                1695

Gly Ala Gly Lys Thr Arg Arg Val Leu Pro Glu Ile Val Arg Glu
1700                1705                1710

Ala Ile Lys Lys Arg Leu Arg Thr Val Ile Leu Ala Pro Thr Arg
1715                1720                1725

Val Val Ala Ala Glu Met Glu Glu Ala Leu Arg Gly Leu Pro Val
1730                1735                1740

Arg Tyr Met Thr Thr Ala Val Asn Val Thr His Ser Gly Thr Glu
1745                1750                1755

Ile Val Asp Leu Met Cys His Ala Thr Phe Thr Ser Arg Leu Leu
1760                1765                1770

Gln Pro Ile Arg Val Pro Asn Tyr Asn Leu Tyr Ile Met Asp Glu
1775                1780                1785

Ala His Phe Thr Asp Pro Ser Ser Ile Ala Ala Arg Gly Tyr Ile
1790                1795                1800

Ser Thr Arg Val Glu Met Gly Glu Ala Ala Ala Ile Phe Met Thr
1805                1810                1815

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys Asn Gln Glu Trp Asp Phe Val
1895                1900                1905

Ile Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Met Tyr Gly Gly Gly Cys Ala Glu Thr Asp
1970                1975                1980

Glu Gly His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
```

```
                 2030                2035                2040
Pro Val Trp Leu Ala Tyr Gln Val Ala Ser Ala Gly Ile Thr Tyr
    2045                2050                2055
Thr Asp Arg Arg Trp Cys Phe Asp Gly Thr Thr Asn Asn Thr Ile
    2060                2065                2070
Met Glu Asp Ser Val Pro Ala Glu Val Trp Thr Lys Tyr Gly Glu
    2075                2080                2085
Lys Arg Val Leu Lys Pro Arg Trp Met Asp Ala Arg Val Cys Ser
    2090                2095                2100
Asp His Ala Ala Leu Lys Ser Phe Lys Glu Phe Ala Ala Gly Lys
    2105                2110                2115
Arg Gly Ala Ala Leu Gly Val Met Glu Ala Leu Gly Thr Leu Pro
    2120                2125                2130
Gly His Met Thr Glu Arg Phe Gln Glu Ala Ile Asp Asn Leu Ala
    2135                2140                2145
Val Leu Met Arg Ala Glu Thr Gly Ser Arg Pro Tyr Lys Ala Ala
    2150                2155                2160
Ala Ala Gln Leu Pro Glu Thr Leu Glu Thr Ile Met Leu Leu Gly
    2165                2170                2175
Leu Leu Gly Thr Val Ser Leu Gly Ile Phe Phe Val Leu Met Arg
    2180                2185                2190
Asn Lys Gly Ile Gly Lys Met Gly Phe Gly Met Val Thr Leu Gly
    2195                2200                2205
Ala Ser Ala Trp Leu Met Trp Leu Ser Glu Ile Glu Pro Ala Arg
    2210                2215                2220
Ile Ala Cys Val Leu Ile Val Val Phe Leu Leu Leu Val Val Leu
    2225                2230                2235
Ile Pro Glu Pro Glu Lys Gln Arg Ser Pro Gln Asp Asn Gln Met
    2240                2245                2250
Ala Ile Ile Ile Met Val Ala Val Gly Leu Leu Gly Leu Ile Thr
    2255                2260                2265
Ala Asn Glu Leu Gly Trp Leu Glu Arg Thr Lys Asn Asp Ile Ala
    2270                2275                2280
His Leu Met Gly Arg Arg Glu Glu Gly Ala Thr Met Gly Phe Ser
    2285                2290                2295
Met Asp Ile Asp Leu Arg Pro Ala Ser Ala Trp Ala Ile Tyr Ala
    2300                2305                2310
Ala Leu Thr Thr Leu Ile Thr Pro Ala Val Gln His Ala Val Thr
    2315                2320                2325
Thr Ser Tyr Asn Asn Tyr Ser Leu Met Ala Met Ala Thr Gln Ala
    2330                2335                2340
Gly Val Leu Phe Gly Met Gly Lys Gly Met Pro Phe Tyr Ala Trp
    2345                2350                2355
Asp Leu Gly Val Pro Leu Leu Met Met Gly Cys Tyr Ser Gln Leu
    2360                2365                2370
Thr Pro Leu Thr Leu Ile Val Ala Ile Ile Leu Leu Val Ala His
    2375                2380                2385
Tyr Met Tyr Leu Ile Pro Gly Leu Gln Ala Ala Ala Ala Arg Ala
    2390                2395                2400
Ala Gln Lys Arg Thr Ala Ala Gly Ile Met Lys Asn Pro Val Val
    2405                2410                2415
Asp Gly Ile Val Val Thr Asp Ile Asp Thr Met Thr Ile Asp Pro
    2420                2425                2430
```

```
Gln Val Glu Lys Lys Met Gly Gln Val Leu Leu Ile Ala Val Ala
    2435            2440                2445

Ile Ser Ser Ala Val Leu Leu Arg Thr Ala Trp Gly Trp Gly Glu
    2450            2455                2460

Ala Gly Ala Leu Ile Thr Ala Ala Thr Ser Thr Leu Trp Glu Gly
    2465            2470                2475

Ser Pro Asn Lys Tyr Trp Asn Ser Ser Thr Ala Thr Ser Leu Cys
    2480            2485                2490

Asn Ile Phe Arg Gly Ser Tyr Leu Ala Gly Ala Ser Leu Ile Tyr
    2495            2500                2505

Thr Val Thr Arg Asn Ala Gly Leu Val Lys Arg Arg Gly Gly Gly
    2510            2515                2520

Thr Gly Glu Thr Leu Gly Glu Lys Trp Lys Ala Arg Leu Asn Gln
    2525            2530                2535

Met Ser Ala Leu Glu Phe Tyr Ser Tyr Lys Lys Ser Gly Ile Thr
    2540            2545                2550

Glu Val Cys Arg Glu Glu Ala Arg Arg Ala Leu Lys Asp Gly Val
    2555            2560                2565

Ala Thr Gly Gly His Ala Val Ser Arg Gly Ser Ala Lys Leu Arg
    2570            2575                2580

Trp Leu Val Glu Arg Gly Tyr Leu Gln Pro Tyr Gly Lys Val Val
    2585            2590                2595

Asp Leu Gly Cys Gly Arg Gly Gly Trp Ser Tyr Tyr Ala Ala Thr
    2600            2605                2610

Ile Arg Lys Val Gln Glu Val Arg Gly Tyr Thr Lys Gly Gly Pro
    2615            2620                2625

Gly His Glu Glu Pro Met Leu Val Gln Ser Tyr Gly Trp Asn Ile
    2630            2635                2640

Val Arg Leu Lys Ser Gly Val Asp Val Phe His Met Ala Ala Glu
    2645            2650                2655

Pro Cys Asp Thr Leu Leu Cys Asp Ile Gly Glu Ser Ser Ser Ser
    2660            2665                2670

Pro Glu Val Glu Glu Thr Arg Thr Leu Arg Val Leu Ser Met Val
    2675            2680                2685

Gly Asp Trp Leu Glu Lys Arg Pro Gly Ala Phe Cys Ile Lys Val
    2690            2695                2700

Leu Cys Pro Tyr Thr Ser Thr Met Met Glu Thr Met Glu Arg Leu
    2705            2710                2715

Gln Arg Arg His Gly Gly Gly Leu Val Arg Val Pro Leu Ser Arg
    2720            2725                2730

Asn Ser Thr His Glu Met Tyr Trp Val Ser Gly Ala Lys Ser Asn
    2735            2740                2745

Ile Ile Lys Ser Val Ser Thr Thr Ser Gln Leu Leu Leu Gly Arg
    2750            2755                2760

Met Asp Gly Pro Arg Arg Pro Val Lys Tyr Glu Glu Asp Val Asn
    2765            2770                2775

Leu Gly Ser Gly Thr Arg Ala Val Ala Ser Cys Ala Glu Ala Pro
    2780            2785                2790

Asn Met Lys Ile Ile Gly Arg Arg Ile Glu Arg Ile Arg Asn Glu
    2795            2800                2805

His Ala Glu Thr Trp Phe Leu Asp Glu Asn His Pro Tyr Arg Thr
    2810            2815                2820
```

```
Trp Ala Tyr His Gly Ser Tyr Glu Ala Pro Thr Gln Gly Ser Ala
2825            2830            2835

Ser Ser Leu Val Asn Gly Val Val Arg Leu Leu Ser Lys Pro Trp
2840            2845            2850

Asp Val Val Thr Gly Val Thr Gly Ile Ala Met Thr Asp Thr Thr
2855            2860            2865

Pro Tyr Gly Gln Gln Arg Val Phe Lys Glu Lys Val Asp Thr Arg
2870            2875            2880

Val Pro Asp Pro Gln Glu Gly Thr Arg Gln Val Met Asn Ile Val
2885            2890            2895

Ser Ser Trp Leu Trp Lys Glu Leu Gly Lys Arg Lys Arg Pro Arg
2900            2905            2910

Val Cys Thr Lys Glu Glu Phe Ile Asn Lys Val Arg Ser Asn Ala
2915            2920            2925

Ala Leu Gly Ala Ile Phe Glu Glu Lys Glu Trp Lys Thr Ala
2930            2935            2940

Val Glu Ala Val Asn Asp Pro Arg Phe Trp Ala Leu Val Asp Arg
2945            2950            2955

Glu Arg Glu His His Leu Arg Gly Glu Cys His Ser Cys Val Tyr
2960            2965            2970

Asn Met Met Gly Lys Arg Glu Lys Lys Gln Gly Glu Phe Gly Lys
2975            2980            2985

Ala Lys Gly Ser Arg Ala Ile Trp Tyr Met Trp Leu Gly Ala Arg
2990            2995            3000

Phe Leu Glu Phe Glu Ala Leu Gly Phe Leu Asn Glu Asp His Trp
3005            3010            3015

Met Gly Arg Glu Asn Ser Gly Gly Gly Val Glu Gly Leu Gly Leu
3020            3025            3030

Gln Arg Leu Gly Tyr Ile Leu Glu Glu Met Asn Arg Ala Pro Gly
3035            3040            3045

Gly Lys Met Tyr Ala Asp Asp Thr Ala Gly Trp Asp Thr Arg Ile
3050            3055            3060

Ser Lys Phe Asp Leu Glu Asn Glu Ala Leu Ile Thr Asn Gln Met
3065            3070            3075

Glu Glu Gly His Arg Thr Leu Ala Leu Ala Val Ile Lys Tyr Thr
3080            3085            3090

Tyr Gln Asn Lys Val Val Lys Val Leu Arg Pro Ala Glu Gly Gly
3095            3100            3105

Lys Thr Val Met Asp Ile Ile Ser Arg Gln Asp Gln Arg Gly Ser
3110            3115            3120

Gly Gln Val Val Thr Tyr Ala Leu Asn Thr Phe Thr Asn Leu Val
3125            3130            3135

Val Gln Leu Ile Arg Asn Met Glu Ala Glu Glu Val Leu Glu Met
3140            3145            3150

Gln Asp Leu Trp Leu Leu Arg Lys Pro Glu Lys Val Thr Arg Trp
3155            3160            3165

Leu Gln Ser Asn Gly Trp Asp Arg Leu Lys Arg Met Ala Val Ser
3170            3175            3180

Gly Asp Asp Cys Val Val Lys Pro Ile Asp Asp Arg Phe Ala His
3185            3190            3195

Ala Leu Arg Phe Leu Asn Asp Met Gly Lys Val Arg Lys Asp Thr
3200            3205            3210

Gln Glu Trp Lys Pro Ser Thr Gly Trp Ser Asn Trp Glu Glu Val
```

```
                3215                3220                3225
Pro Phe Cys Ser His His Phe Asn Lys Leu Tyr Leu Lys Asp Gly
            3230                3235                3240
Arg Ser Ile Val Val Pro Cys Arg His Gln Asp Glu Leu Ile Gly
            3245                3250                3255
Arg Ala Arg Val Ser Pro Gly Ala Gly Trp Ser Ile Arg Glu Thr
            3260                3265                3270
Ala Cys Leu Ala Lys Ser Tyr Ala Gln Met Trp Gln Leu Leu Tyr
            3275                3280                3285
Phe His Arg Arg Asp Leu Arg Leu Met Ala Asn Ala Ile Cys Ser
            3290                3295                3300
Ala Val Pro Val Asp Trp Val Pro Thr Gly Arg Thr Thr Trp Ser
            3305                3310                3315
Ile His Gly Lys Gly Glu Trp Met Thr Thr Glu Asp Met Leu Met
            3320                3325                3330
Val Trp Asn Arg Val Trp Ile Glu Glu Asn Asp His Met Glu Asp
            3335                3340                3345
Lys Thr Pro Val Thr Lys Trp Thr Asp Ile Pro Tyr Leu Gly Lys
            3350                3355                3360
Arg Glu Asp Leu Trp Cys Gly Ser Leu Ile Gly His Arg Pro Arg
            3365                3370                3375
Thr Thr Trp Ala Glu Asn Ile Lys Asp Thr Val Asn Met Val Arg
            3380                3385                3390
Arg Ile Ile Gly Asp Glu Glu Lys Tyr Met Asp Tyr Leu Ser Thr
            3395                3400                3405
Gln Val Arg Tyr Leu Gly Glu Glu Gly Ser Thr Pro Gly Val Leu
            3410                3415                3420

<210> SEQ ID NO 6
<211> LENGTH: 10807
<212> TYPE: DNA
<213> ORGANISM: Artificial Sequence
<220> FEATURE:
<223> OTHER INFORMATION: Synthetic Genomic sequence of the chimeric
      ZIKALIVax virus (10,807 nt; 3,423 aa):

<400> SEQUENCE: 6
agttgttgat ctgtgtgagt cagactgcga cagttcgagt ctgaagcgag agctaacaac    60
agtatcaaca ggtttaattt ggatttggaa acgagagttt ctggtcatga aaacccaaa    120
aaagaaatcc ggaggattcc ggattgtcaa tatgctaaaa cgcggagtag cccgtgtgag   180
ccccttgggg ggcttgaaga ggctgccagc cggacttctg ctgggtcatg ggcccatcag   240
gatggtcttg gcgattctag cctttttgag attcacggca atcaagccat cactgggtct   300
catcaataga tggggttcag ttgggaaaaa agaggctatg gaaataataa agaagttcaa   360
gaaagatctg gctgccatgc tgagaataat caatgctagg aaggagaaga gagacgagg   420
cgcagatact agtgtcggaa ttgttggcct cctgctgacc acagctatgg cagcggaggt   480
cactagacgt gggagtgcat actatatgta cttggacaga acgatgctg gggaggccat   540
atctttttcca accacattgg ggatgaataa gtgttatata cagatcatgg atcttggaca   600
catgtgtgat gccaccatga gctatgaatg ccctatgctg gatgaggggg tggaaccaga   660
tgacgtcgat tgttggtgca acacgacgtc aacttgggtt gtgtacggaa cctgccatca   720
caaaaaggt gaagcacgga gatctagaag agctgtgacg ctccccctcc attccactag   780
gaagctgcaa acgcggtcgc aaacctggtt ggaatcaaga gaatacacaa agcacttgat   840
```

```
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttgggttg atgttgtctt ggaacatgga ggttgtgtca ccgtaatggc   1080
acaggacaaa ccgactgtcg acatagagct ggttacaaca acagtcagca acatggcgga   1140
ggtacgatcg tactgctatg aggcatcaat atcagacatg gcttcggaca gccgctgccc   1200
aacacaaggt gaagcctacc ttgacaagca atcagacact caatatgtct gcaaaagaac   1260
gttagtggac agaggctggg gaaatggatg tggactttt ggcaaaggga gcctggtgac    1320
atgcgctaag tttgcatgct ccaagaaaat gaccgggaag agcatccagc cagagaatct   1380
ggagtaccgg ataatgctgt cagttcatgg ctcccagcac agtgggatga ctgtcaatga   1440
tataggatat gaaactgatg agaatagagc gaaagttgag ataacgccca attccaccaag  1500 agccgaagcc accctggggg gttttggaag cctaggactt gattgtgaac cgaggacagg   1560
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaagaagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc ctctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgaccccagt   2040
tgggaggttg ataaccgcta accccgtaat cactgaaagc actgagaact ctaagatgat   2100
gctggaactt gatccaccat ttggggactc ttacattgtc ataggagtcg gggagaagaa   2160
gatcacccac cactggcaca ggagtggcag caccattgga aaagcatttg aggccactgt   2220
gagaggcgcc aagagaatgg cagtcctggg ggatacagcc tggacttcg gatcagtcgg   2280 gggtgtgttc aactcactgg gtaagggcat tcaccagatt tttggagcag ccttcaaatc   2340
actgtttgga ggaatgtcct ggttctcaca gatcctcata ggcacgctgc tagtgtggtt   2400
aggtttgaac acaaagaatg gatctatctc cctcacatgc ttggcctggg gggagtgat    2460 gatcttcctc tccacggctg tttctgctga cgtggggtgc tcagtggact ctcaaaaaaa   2520
ggaaacgaga tgtggcacgg gggtattcat ctataatgat gttgaagcct ggagggaccg   2580
gtacaagtac catcctgact cccccgcag attggcagca gcagtcaagc aggcctggga   2640 agagggatc tgtgggatct catccgtttc aagaatggaa acatcatgt ggaaatcagt    2700 agaaggggag ctcaatgcta tcctagagga gaatggagtt caactgacag ttgttgtggg   2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acactgaa ggaatgtccg cttgagcaca gagcatggaa     2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa acatgtgaa tggccaaagt ctcacacatt     3180
```

```
gtggacagat ggagtagaag aaagtgatct tatcatacac aagtctttag ctggtccact    3240
cagccaccac aacaccagag agggttacag aacccaagtg aaagggccat ggcacagtga    3300
agagcttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtctcc ttcattttca gagccaattg    3840
acacccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agaccctatt aatgtggtag actactgtt    4200
actcacaagg agtgggaagc ggagctggcc ccctagtgaa gttctcacag ccgttggcct    4260
gatatgtgca ctgccggag gtttgccaa ggcagacatt gagatggctg acccatggc    4320
tgcagtaggc ttgctaattg tcagctatgt ggtctcggga aagagtgtgg acatgtacat    4380
tgaaagagca ggtgacatca catgggaaaa ggacgcggaa gtcactggaa acagtcctcg    4440
gcttgacgtg gcactggatg agagtggtga tttctccttg gtagaggaag atggtccacc    4500
catgagagag atcatactta aggtggtcct gatggccatc tgtggcatga acccaatagc    4560
tataccttt gctgcaggag cgtggtatgt gtatgtgaag actgggaaaa ggagtggcgc    4620
cctctgggac gtgcctgctc ccaaagaagt gaagaaagga gagaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acgggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc caggggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaagagaa ctccggacag tgatcttggc    5280
accaactagg gttgtcgctg ctgagatgga ggaggcttg agaggacttc cggtgcgtta    5340
catgacaaca gcagtcaacg tcacccattc tgggacagaa atcgttgatt tgatgtgcca    5400
tgccactttc acttcacgct actacaacc catcagagtc cctaattaca atctctacat    5460
catggatgaa gcccacttca cagaccctc aagtatagct gcaagaggat atatatcaac    5520
aagggttgaa atgggcgagg cggctgccat ttttatgact gccacaccac caggaaccg    5580
```

```
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg aaagcgggt    5760 catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagaggag accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca agaattcgc cgctggaaaa agaggagcgg ctttgggagt    6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagatgggct ttggaatggt   6720 aaccccttggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct    6960
aatgggaagg agagaagaag gagcaaccat gggattctca atggacattg atctgcggcc   7020
agcctccgcc tgggctatct atgccgcatt gacaactctc atcaccccag ctgtccaaca   7080
tgcggtaacc acttcataca acaactactc cttaatggcg atggccacac aagctggagt   7140
gctgtttggc atgggcaaag gatgccatt ttatgcatgg gaccttggag tcccgctgct    7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag accccaggt ggagaagaag atgggacaag tgttactcat    7440
agcagtagcc atctccagtg ctgtgctgct gcggaccgcc tggggatggg gggaggctgg   7500
agctctgatc acagcagcga cctccacctt gtgggaaggc tctccaaaca atactggaa    7560 ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag acatgccgt atcccgggga agtgcaaagc tcagatggtt    7860
ggtggagaga ggatatctgc agcctatgg gaaggttgtt gacctcggat gtggcagagg   7920
```

```
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accagggggcc ttctgtataa aggtgctgtg   8220
cccatacacc agcactatga tggaaaccat ggagcgactg caacgtaggc atggggaggg   8280
attagtcaga gtgccattgt ctcgcaactc cacacatgag atgtactggg tctctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catcagaaaa catggtttct tgatgaaaac cacccataca ggacatgggc    8580
ctaccatggg agctacgaag ccccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga gagaaaaaa gaatggaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga agcaaggaga    9060
gttcgggaaa gcaaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc cagagaaagt    9600
gaccagatgg ttgcagagca atggatggga tagactcaaa cgaatggcgg tcagtggaga    9660
tgactgcgtt gtgaagccaa tcgatgatag gttttgcacat gccctcaggt tcttgaatga    9720
catgggaaaa gttaggaaag acacacagga gtggaacccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960
gctcctttat ttccacagaa gagaccttcg actgatggct aatgccattt gctcggctgt   10020
gccagttgac tgggtaccaa ctgggagaac cacctggtca atccatggaa agggagaatg   10080
gatgaccact gaggacatgc tcatggtgtg gaatagagtg tggattgagg agaacgacca   10140
tatggaggac aagactcctg taacaaaatg gacagacatt ccctatctag gaaaagggga   10200
ggacttatgt gtggatcccc ttataggggca cagaccccgc accacttggg ctgaaaacat   10260
caaagacaca gtcaacatgg tgcgcaggat cataggtgat gaagaaaagt acatggacta   10320
```

```
tctatccacc caagtccgct acttgggtga ggaagggtcc acacccggag tgttgtaagc    10380 accaattta gtgttgtcag gcctgctagt cagccacagt ttggggaaag ctgtgcagcc    10440
tgtaaccccc ccaggagaag ctgggaaacc aagctcatag tcaggccgag aacgccatgg    10500
cacggaagaa gccatgctgc ctgtgagccc ctcagaggac actgagtcaa aaaccccac    10560 gcgcttggaa gcgcaggatg ggaaaagaag gtggcgacct tccccacccct tcaatctggg   10620 gcctgaactg gagactagct gtgaatctcc agcagaggga ctagtggtta gaggagaccc    10680
cccggaaaac gcaaaacagc atattgacgc tgggaaagac cagagactcc atgagtttcc    10740
accacgctgg ccgccaggca cagatcgccg aacagcggcg gccggtgtgg ggaaatccat    10800
ggtttct                                                              10807
```

<210> SEQ ID NO 7
<211> LENGTH: 1512
<212> TYPE: DNA
<213> ORGANISM: Artificial Sequence
<220> FEATURE:
<223> OTHER INFORMATION: Synthetic Sequences of the E gene from chimeric
      ZIKALIVax virus (1512 nt; 504 aa)

<400> SEQUENCE: 7

```
atcaggtgca taggagtcag caatagggac tttgtggaag gtatgtcagg tgggacttgg      60
gttgatgttg tcttggaaca tggaggttgt gtcaccgtaa tggcacagga caaaccgact     120
gtcgacatag agctggttac aacaacagtc agcaacatgg cggaggtacg atcgtactgc     180
tatgaggcat caatatcaga catggcttcg gacagccgct gcccaacaca aggtgaagcc     240
taccttgaca agcaatcaga cactcaatat gtctgcaaaa gaacgttagt ggacagaggc     300
tggggaaatg gatgtggact ttttggcaaa gggagcctgg tgacatgcgc taagtttgca     360
tgctccaaga aaatgaccgg gaagagcatc cagccagaga atctggagta ccggataatg     420
ctgtcagttc atggctccca gcacagtggg atgactgtca atgatatagg atatgaaact     480
gatgagaata gagcgaaagt tgagataacg cccaattcac caagagccga agccaccctg     540
gggggttttg gaagcctagg acttgattgt gaaccgagga caggccttga cttttcagat     600
ttgtattact tgactatgaa taacaagcac tggttggttc acaaggagtg gttccacgac     660
attccattac cttggcacgc tggggcagac accggaactc cacactggaa caacaaagaa     720
gcactggtag agttcaagga cgcacatgcc aaaaggcaaa ctgtcgtggt tctagggagt     780
caagaaggag cagttcacac ggcccttgct ggagctctgg aggctgagat ggatggtgca     840
aagggaaggc tgtcctctgg ccacttgaaa tgtcgcctga aaatggataa acttagattg     900
aagggcgtgt catactcctt tgtgtactgc agcgttcacat tcaccaagat cccggctgaa     960
acactgcacg gacagtcac agtggaggta cagtacgcag ggacagatgg accttgcaag    1020
gttccagctc agatggcggt ggacatgcaa actctgaccc cagttgggag gttgataacc    1080
gctaaccccg taatcactga agcactgag aactctaaga tgatgctgga acttgatcca    1140
ccatttgggg actcttacat tgtcatagga gtcgggagga gaagatcac ccaccactgg    1200 cacaggagtg gcagcaccat tggaaaagca tttgaggcca ctgtgagagg cgccaagaga    1260
atggcagtcc tggggataca agcctgggac ttcggatcag tcggggtgt gttcaactca    1320
```

```
ctgggtaagg gcattcacca gatttttgga gcagccttca aatcactgtt tggaggaatg    1380
tcctggttct cacagatcct cataggcacg ctgctagtgt ggttaggttt gaacacaaag    1440
aatggatcta tctccctcac atgcttggcc ctgggggggag tgatgatctt cctctccacg    1500
gctgtttctg ct                                                         1512
```

VACCINE COMPOSITIONS COMPRISING AN ATTENUATED MUTANT ZIKA VIRUS

FIELD OF THE INVENTION

The present invention relates to vaccine compositions comprising an attenuated mutant Zika virus.

BACKGROUND OF THE INVENTION

Zika virus is a mosquito-borne flavivirus that was first identified in Uganda in 1947 in monkeys through a network that monitored yellow fever. It was later identified in humans in 1952 in Uganda and the United Republic of Tanzania. Outbreaks of Zika virus disease have been recorded in Africa, the Americas, Asia and the Pacific. From the 1960s to 1980s, human infections were found across Africa and Asia, typically accompanied by mild illness. The first large outbreak of disease caused by Zika infection was reported from the Island of Yap (Federated States of Micronesia) in 2007. In July 2015 Brazil reported an association between Zika virus infection and Guillain-Barré syndrome. In October 2015 Brazil reported an association between Zika virus infection and microcephaly. Zika virus is primarily transmitted to people through the bite of an infected mosquito from the *Aedes* genus, mainly *Aedes aegypti* in tropical regions. *Aedes* mosquitoes usually bite during the day, peaking during early morning and late afternoon/evening. This is the same mosquito that transmits Zika virus, chikungunya and yellow fever. Sexual transmission of Zika virus is also possible. Other modes of transmission such as blood transfusion are being investigated. Zika virus disease is usually mild and requires no specific treatment. People sick with Zika virus should get plenty of rest, drink enough fluids, and treat pain and fever with common medicines. If symptoms worsen, they should seek medical care and advice. There is currently no vaccine available. WHO experts have suggested that the priority should be to develop attenuated vaccines and other non-live vaccines, which are safe to use in pregnant women and those of childbearing age.

SUMMARY OF THE INVENTION

The present invention relates to vaccine compositions comprising an attenuated mutant Zika virus. In particular, the present invention is defined by the claims.

DETAILED DESCRIPTION OF THE INVENTION

The present invention relates to an attenuated mutant Zika virus that provides the advantages of to be safe in particular for vaccinating pregnant women. In particular, the inventors have introduced mutations at very specific positions that abrogate the N-glycosylation site on the E protein of the epidemic strain which will prevent the generation of autoantibodies responsible for Guillain-Barré syndrome. Moreover, the inventors have produced additional mutations of the virus that result to a dramatic reduction of the cytopathic effects without affecting the capacity to produce high titers of virus.

Accordingly, the first object of the present invention relates to an attenuated mutant Zika virus comprising a protein E of the epidemic strain wherein at least one amino acid residue at position 152, 156 or 158 is mutated.

As used herein, the term "attenuated" has its general leaning in the art and in particular to a virus rendered less virulent. In particular the attenuated mutant Zika virus of the present invention is non non-pathogenic. As used herein, the term "non-pathogenic" is used herein to mean non-virulent or unable to induce illness in particular Guillain-Barré syndrome. As used herein the term "Zika virus" has its general meaning in the art. The Zika virus is a positive sense single-stranded RNA molecule 10794 bases long with two non-coding regions flanking regions known as the 5' NCR and the 3' NCR. The open reading frame of the Zika virus codes for a polyprotein that is subsequently cleaved into capsid (C), precursor membrane (prM), envelope (E), and non-structural proteins (NS). The E protein composes the majority of the virion surface and is involved with aspects of replication such as host cell binding and membrane fusion. NS1, NS3, and NS5 are large, highly-conserved proteins while the NS2A, NS2B, NS4A, and NS4B proteins are smaller, hydrophobic proteins. Located in the 3' NCR are 428 nucleotides that may play a part in translation, RNA packaging, cyclization, genome stabilization, and recognition. The 3' NCR forms a loop structure and the 5' NCR allows translation via a methylated nucleotide cap or a genome-linked protein.

The term "epidemic strain" refers to the Zika strain responsible for the epidemic infections. In particular, the epidemic strain is characterized by having a protein E having at least 98% of identity with the amino acid sequence represented by SEQ ID NO:1. In some embodiments, the epidemic Zika strain refers to the Zika strain BeH819015 (Genbank # KU365778).

Accordingly, in some embodiments, the present invention relates to an attenuated mutant Zika virus comprising a protein E consisting of the amino acid sequence having at least 98% of identity with SEQ ID NO:1 wherein at least one amino acid residue at position 152, 156 or 158 is mutated.

According to the invention a first amino acid sequence having at least 98% of identity with a second amino acid sequence means that the first sequence has 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

As used herein, the term mutation has its general meaning in the art and refers to a substitution, deletion or insertion. The term "substitution" means that a specific amino acid residue at a specific position is removed and another amino acid residue is inserted into the same position. The term "deletion" means that a specific amino acid residue is removed. The term "insertion" means that one or more amino acid residues are inserted before or after a specific amino acid residue, more specifically, that one or more, preferably one or several, amino acid residues are bound to an a.-carboxyl group or an a,-amino group of the specific amino acid residue.

In some embodiments, the amino acid residue at position 152, 156 or 158 is substituted. In some embodiments, the isoleucine residue (I) at position 152 is substituted by a threonine residue (T). In some embodiments, the threonine residue (T) at position 156 is substituted by an isoleucine residue (I). In some embodiments, the histidine residue (H) is substituted by a tyrosine residue (Y).

In some embodiments, the protein E comprises 2 mutations. In some embodiments, the protein comprises an amino acid sequence wherein the isoleucine residue (I) at position 152 is substituted by a threonine residue (T) and the threonine residue (T) at position 156 is substituted by an isoleucine residue (I). In some embodiments, the protein E comprises 3 mutations. In some embodiments, the protein E comprises an amino acid sequence wherein the isoleucine residue (I) at position 152 is substituted by a threonine residue (T), the threonine residue (T) at position 156 is substituted by an isoleucine residue (I), and the histidine residue (H) is substituted by a tyrosine residue (Y). In some embodiments, the protein E consists of the amino acid sequence represented by SEQ ID NO:2.

In some embodiments, the attenuated mutant Zika virus of the present invention comprises the structural proteins C and prM of the epidemic strain.

In some embodiments, the attenuated mutant Zika virus of the present invention comprises the non-structural proteins of the epidemic strain.

In some embodiments, the attenuated mutant Zika virus of the present invention comprises the structural proteins C and prM of the epidemic strain and the non-structural proteins of the epidemic strain. In some embodiments, the attenuated mutant Zika virus of the present invention is characterized by the genomic sequence encoding for the polyprotein consisting of the amino acid sequence represented by SEQ ID NO:3. In some embodiments, the attenuated mutant Zika virus of the present invention is characterized by the genomic sequence represented by SEQ ID NO:4.

In some embodiments, the attenuated mutant Zika virus of the present invention comprises the non-structural proteins of an endemic strain. As used herein, the term "endemic strain" refers to a Zika strain originated from Africa. In some embodiments, the attenuated mutant Zika virus of the present invention comprises the non-structural proteins of the Zika strain MR 766-NIID* (Genbank # LC002520).

In some embodiments, the attenuated mutant Zika virus of the present invention comprises the structural proteins C and prM of the epidemic strain and the non-structural proteins of the Zika strain MR 766-NIID* (Genbank # LC002520). In some embodiments, the attenuated mutant Zika virus of the present invention is characterized by the genomic sequence encoding for the polyprotein consisting of the amino acid sequence represented by SEQ ID NO:5. In some embodiments, the attenuated mutant Zika virus of the present invention is characterized by the genomic sequence represented by SEQ ID NO:6.

A further object of the present invention relates to an isolated nucleic acid molecule encoding the attenuated mutant Zika virus of the present invention.

In some embodiments, the isolated acid molecule of the present invention comprises a nucleic acid sequence encoding for the mutated protein E of the present invention. In some embodiments, the isolated acid molecule of the present invention comprises a nucleic acid sequence represented by SEQ ID NO:7. In some embodiments, the isolated acid molecule of the present invention comprises a nucleic acid sequence represented by SEQ ID NO:4. In some embodiments, the isolated acid molecule of the present invention comprises a nucleic acid sequence represented by SEQ ID NO:6.

The isolated nucleic acid molecule of the present invention is particular suitable for the production of the attenuated mutant zika virus of the present invention by recombinant DNA technology. Typically, the isolated nucleic acid molecule of the present invention is cloned into standard protein expression vectors and used to infect appropriate host cells. The host cells are then cultured, thus expressing the desired virus, which can be purified to the desired extent and formulated into a suitable vaccine product.

Accordingly a further object of the present invention relates to a host cell comprising the nucleic acid molecule of this invention. The host cell is typically a cell line suitable for propagating the virus. Suitable cell lines include mammalian cells, such as Vero cells, AGMK cells, BHK-21 cells, COS-1 or COS-7 cells, MDCK cells, CV-1 cells, LLC-MK2 cells, primary cell lines such as fetal Rhesus lung (FRhL-2) cells, BSC-1 cells, and MRC-5 cells, or human diploid fibroblasts, as well as avian cells, chicken or duck embryo derived cell lines, e.g., AGE1 cells, and primary, chicken embryo fibroblasts, and mosquito cell lines, such as C6/36. The cultures are fed with medium capable of supporting growth of the cells. The host cells are maintained in culture for several days until the desired virus titer is achieved. Optionally, the cells are maintained in a continuous perfusion system from which virus can be intermittently or continuously obtained over the course of several days or more. Under non-continuous culture conditions, a virus titer of at least about $10^6$ to $10^7$ PFU/ml by 3-7 days post infection, is desirable. To recover virus, the virus is harvested by common methods known in the art including slow-speed centrifugation, or by filtration. Methods for concentrating said virus(es) are within the scope of a person with ordinary skill in the art and include, for example, ultrafiltration, or precipitation with polyethelene glycol (PEG). Methods for purifying viruses are known to a person with ordinary skill in the art and typically include continuous or multi-step sucrose gradients, purification by column chromatography using size exclusion, ion exchange, adsorption, or affinity columns, or purification by partitioning in polymer two-phase or multi-phase systems, and any combination thereof. Methods for assaying for virus positive fractions include plaque assay, hemagglutination (HA) assay, and/or antigen assays such as immunoassays.

In some embodiments, the harvested attenuated mutant Zika virus of the present invention is rendered inactive. As used herein, the term "inactive" encompasses a virus that has been replicated, e.g., in vitro, and then killed using chemical or physical means such that it is no longer capable of replicating. For example, the live attenuated virus can be inactivated, using chemical agents, such as formaldehyde, betapropiolactone (BPL), or hydrogen peroxide, or using ultraviolet irradiation, or by using a combination of two or more inactivation steps (which can be the same or different, e.g., formaldehyde and BPL, formaldehyde and UV irradiation, BPL and UV irradiation, hydrogen peroxide and BPL, hydrogen peroxide and UV irradiation, etc., in any combination).

A further object of the present invention relates to vaccine composition comprising the attenuated Zika virus of the present invention.

As used herein the term "vaccine composition" is a composition suitable for administration to a human is capable of eliciting a specific immune response against a pathogen, such as Zika virus.

The vaccine composition of the present invention comprises an amount of live attenuated Zika virus of the present invention or an amount of inactive attenuated Zika virus of the present invention The vaccine composition of the present invention can also include one or more additional components capable of eliciting or enhancing an immune response, such as an excipient, carrier, and/or adjuvant. An "adjuvant" is an agent that enhances the production of an antigen-specific immune response as compared to administration of the antigen in the absence of the agent. Common adjuvants include aluminum containing adjuvants that include a suspensions of minerals (or mineral salts, such as aluminum hydroxide, aluminum phosphate, aluminum hydroxyphosphate) onto which antigen is adsorbed. In the context of the present disclosure the adjuvants are aluminum-(alum-)free adjuvants, which are formulated in the absence of any such aluminum salts. Alum-free adjuvants include oil and water emulsions, such as water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components. Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or polyoxyethethylene sorbitan monooleate. Alternative so lubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in Remington's Pharmaceutical Sciences, by E. W. Martin, Mack Publishing Co., Easton, Pa., 5th Edition (1975). Accordingly, suitable excipients and carriers can be selected by those of skill in the art to produce a formulation suitable for delivery to a subject by a selected route of administration. Suitable excipients include, without limitation: glycerol, Polyethylene glycol (PEG), Sorbitol, Trehalose, N-lauroylsarcosine sodium salt, L-proline, Non detergent sulfobetaine, Guanidine hydrochloride, Urea, Trimethylamine oxide, KCl, Cat2+, Mg2+, Mn2+, Zn2+ and other divalent cation related salts, Dithiothreitol, Dithioerytrol, and β-mercaptoethanol. Other excipients can be detergents (including: polyoxyethethylene sorbitan monooleate, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide). Preparation of vaccine compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the vaccine composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 0.05-100 μg of inactivated virus, such as from about 0.1 μg (e.g., 0.1, 0.2, 0.3, 0.4, or 0.5 μg) to about 50 μg, for example, from about 0.5 μg to about 30 μg, such as about 1 μg, about 2 μg, about 3 μg, about 4 μg, about 5 μg, about 10 μg, about 15 μg, about 20 μg, or about 25 μg, of each strain of inactivated Zika virus. Typically, the vaccine composition is prepared as injectable, either as liquid solution or suspension; solid form suitable for solution in, or suspension in, liquid prior to injection may also be prepared.

A further object of the present invention relates to a method for eliciting an immune response against Zika virus in a subject comprising administering to the subject a therapeutically effective amount of the vaccine composition of the present invention.

In some embodiments, the vaccine composition of the present invention is administered to an adult or an infant humans. In some embodiments, the vaccine composition of the present invention is administered to a pregnant woman. In some embodiments, the vaccine composition of the present invention is administered to a woman of childbearing age. In some embodiments, the subject was previously exposed to Zika virus.

In some embodiments, the vaccine compostition of the present invention is particularly suitable for the prevention, amelioration or treatment of Zika virus infection and/or Zika virus induced disease.

Although the vaccine composition can be administered by a variety of different routes, most commonly, the vaccine composition is delivered by an intramuscular, subcutaneous or intradermal route of administration. Generally, the vaccine composition may be administered subcutaneously, intradermally, or intramuscularly in a dose effective for the production of neutralizing antibody and protection. The vaccines are administered in a manner compatible with the dosage formulation, and in such amount as will be prophylactically and/or therapeutically effective. The quantity to be administered, which is generally in the range of 0.05-100 μg of virus per dose, depends on the subject to be treated, capacity of the subject's immune system to synthesize antibodies, and the degree of protection desired. Precise amounts of the vaccine to be administered may depend on the judgment of the practitioner and may be peculiar to each subject.

The vaccine composition may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months or years. The dosage regimen will also, at least in part, be determined by the need of the subject and be dependent upon the judgment of the practitioner. Examples of suitable immunization schedules include: a first dose, followed by a second dose between 7 days and 6 months, and an optional third dose between 1 month and two years post initial immunization, or other schedules sufficient to elicit titers of virus-neutralizing antibodies expected to confer protective immunity. The generation of protective immunity against Zika virus with the vaccine composition may reasonably be expected after a primary course of immunization consisting of 1 to 3 inoculations. These could be supplemented by boosters at intervals (e.g., every two years) designed to maintain a satisfactory level of protective immunity.

The invention will be further illustrated by the following figures and examples. However, these examples and figures should not be interpreted in any way as limiting the scope of the present invention.

FIGURES

FIG. 1 shows the different clones of Zika virus

Figures 3, 4:
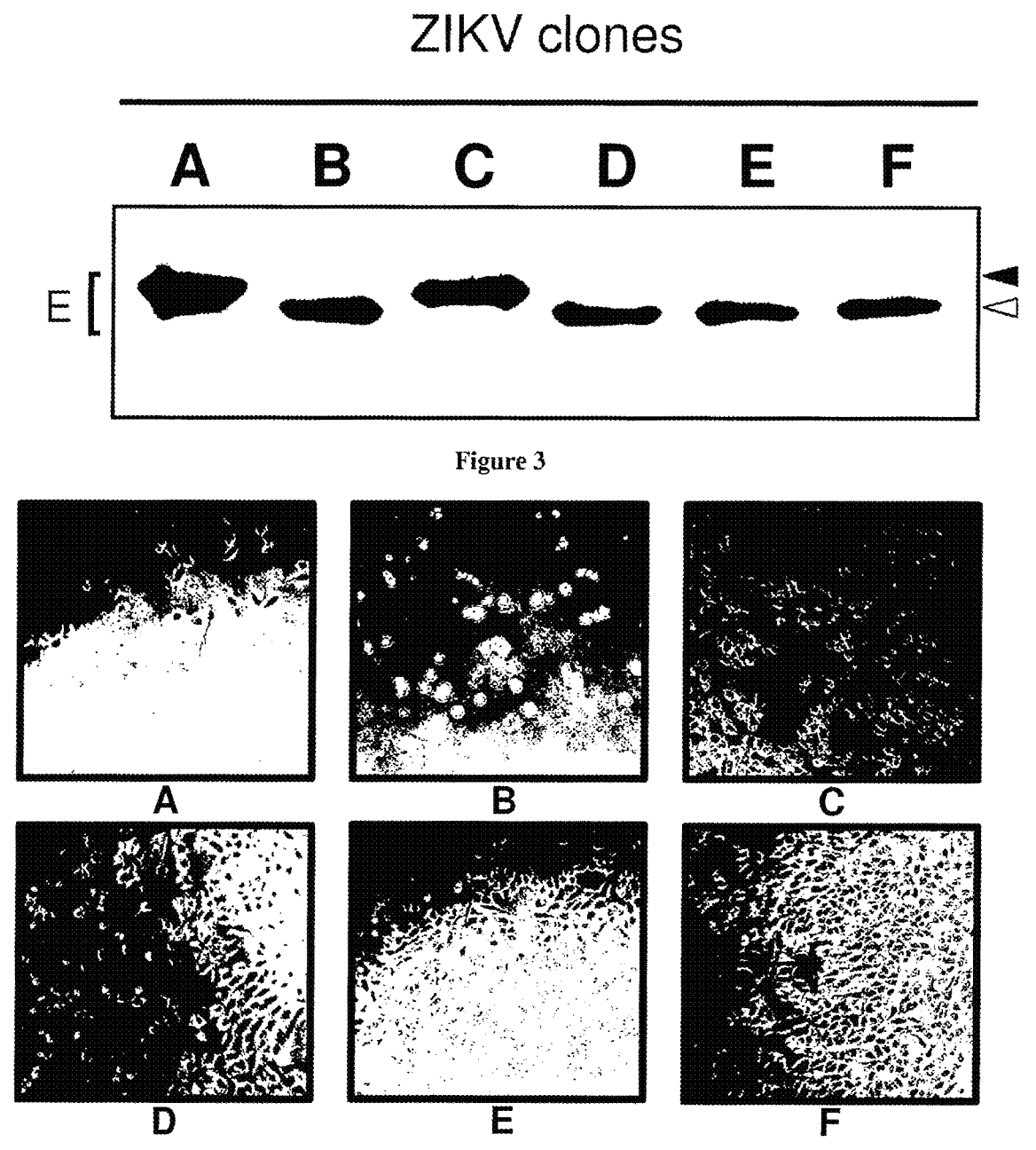

FIG. 3: Processing of the E protein in Vero cells infected with ZIKV clones A to F. Immunoblot assay on cell extracts from Vero cells infected with ZIKV using anti-flavivirus E mAb 4G2. (4-12% SDS-PAGE on non-reducing conditions).

FIG. 4: CPEs in Vero cells infected 72 h with ZIKV clones A to F.

Figure 5:
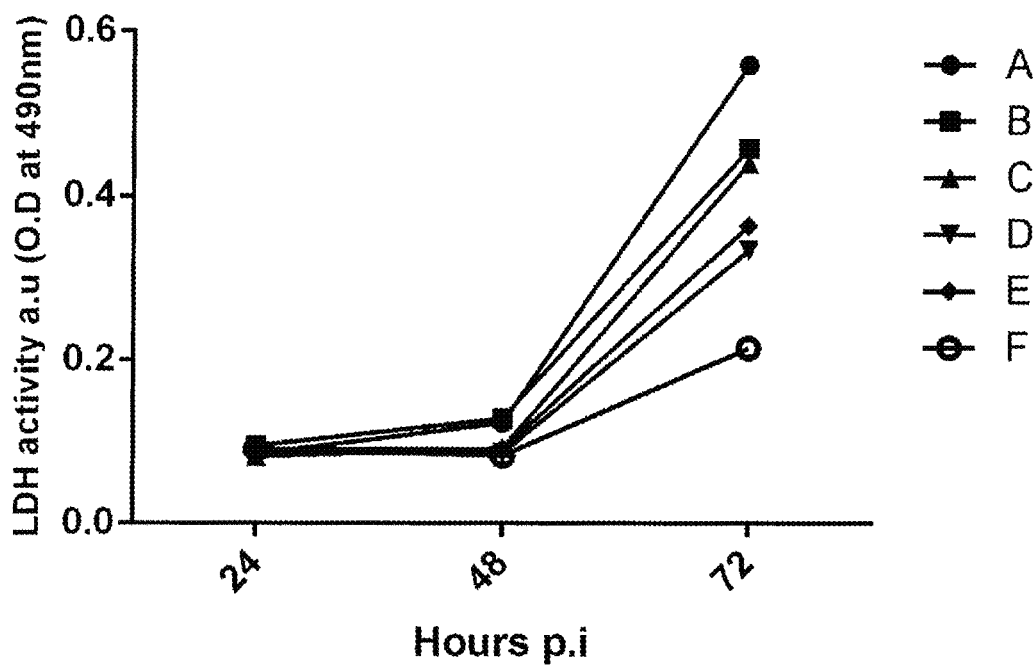

FIG. 5: LDH leakage from Vero cells infected with ZIKV clones A to F

Figure 6:
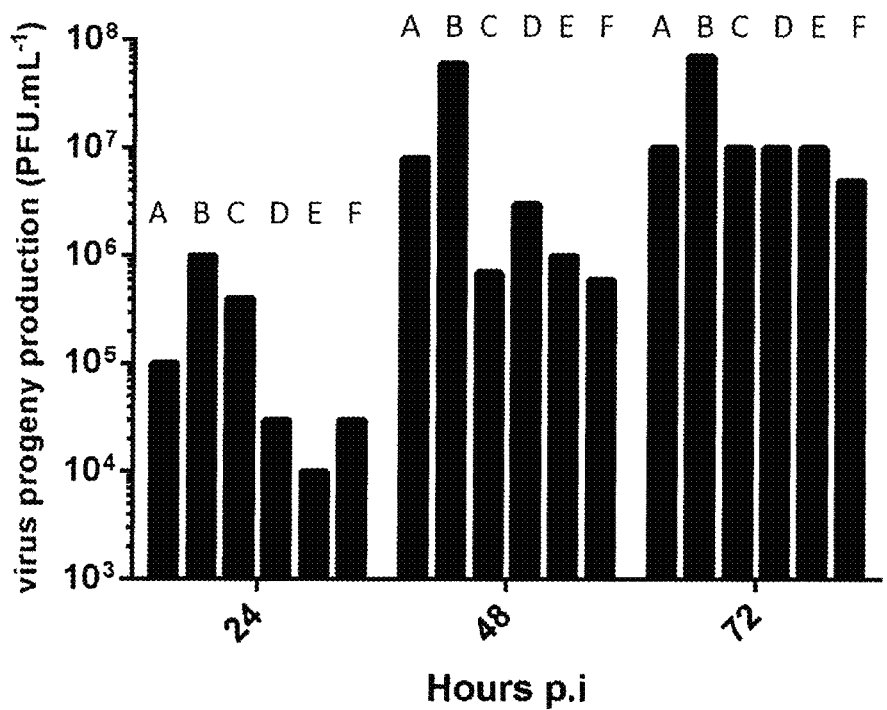

FIG. 6: Progeny virus infection in Vero cells infected with ZIKV clones A to F

EXAMPLE

Figure 1:
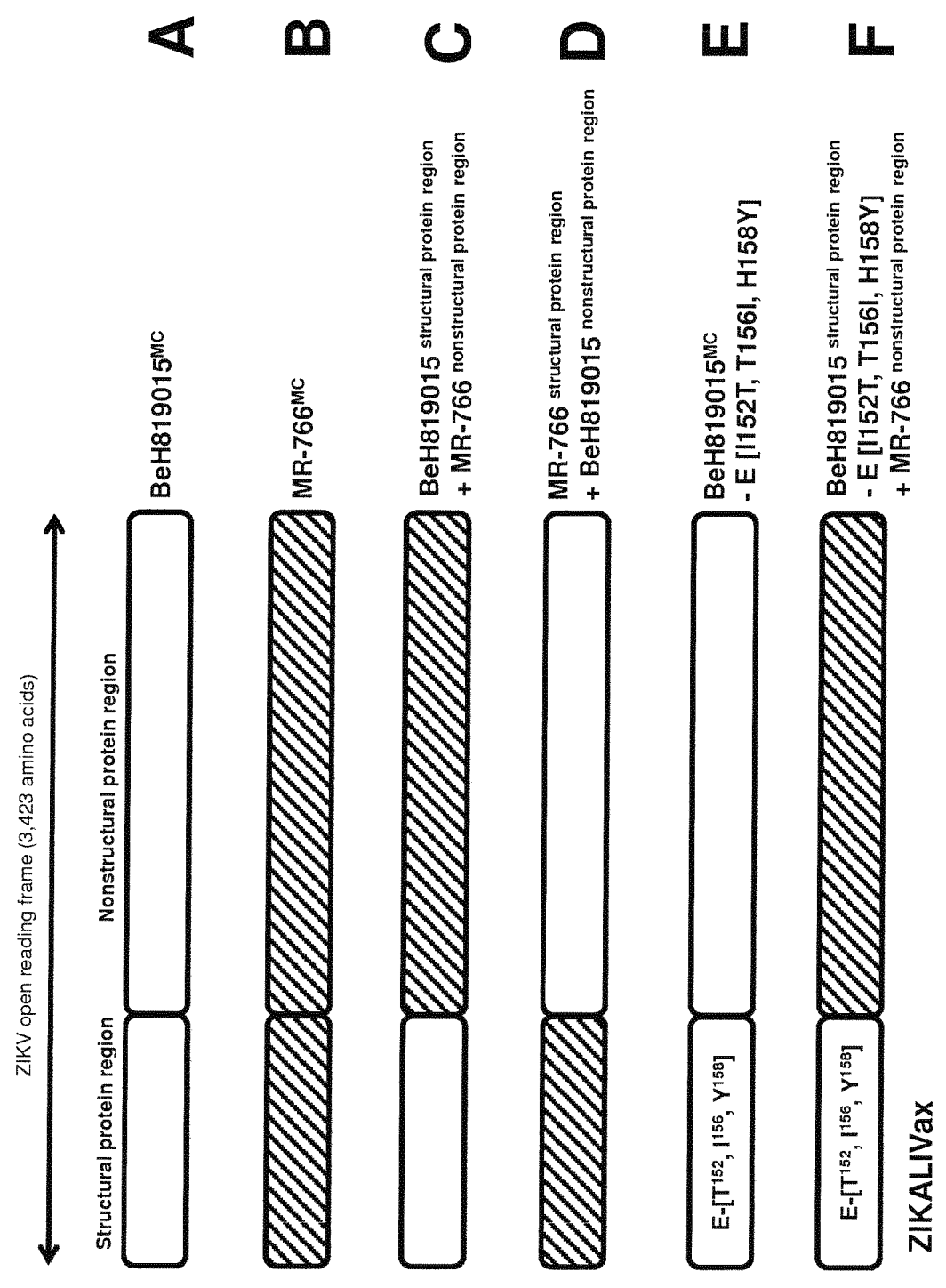
Figure 2:
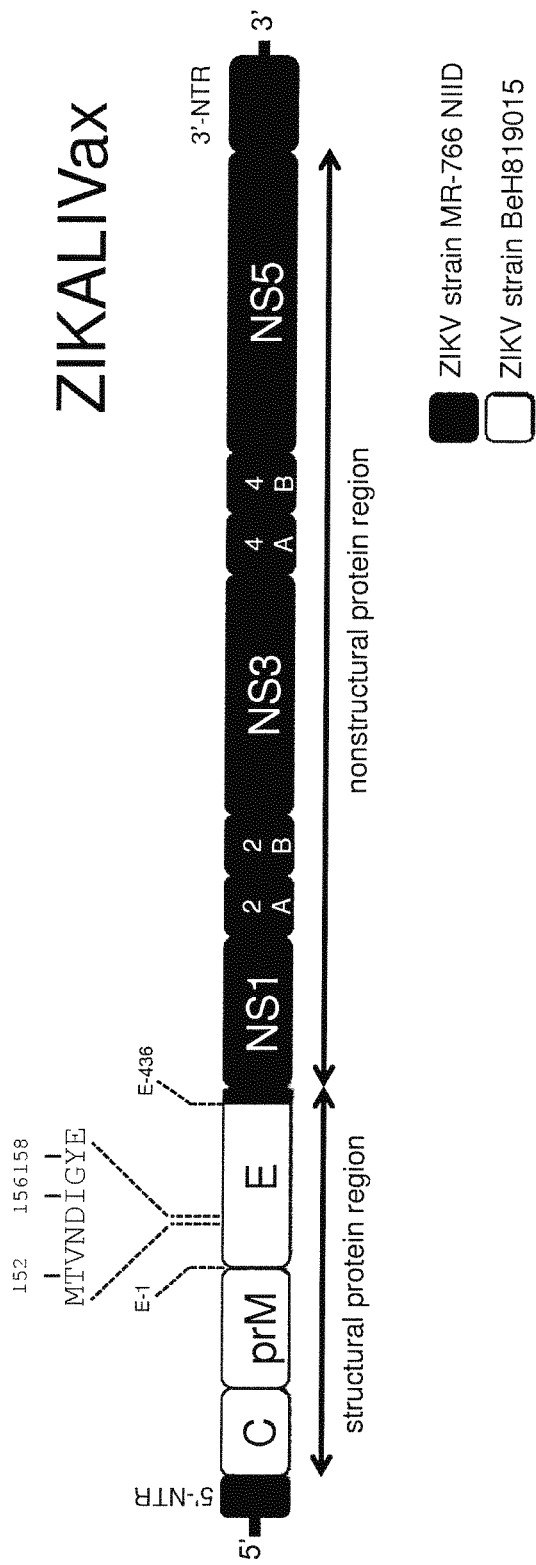
FIG. 2 shows the details of the clone ZIKALIVax

Different clones of Zika virus (A-F) were generated (FIG. 1). Clone F is named "ZIKALIVax" and is detailed in FIG. 2.

Mutations introduced at positions 152, 156, and 158 abrogates N-glycosylation site on the E protein (FIG. 3).

The cytopathic effects of the different clones were tested. Briefly, Vero cells were infected with the different clones at MOI of 0.1 PFU per cell and cytopathic effects were observed at 72 h post-infection by light microscopy. As shown in FIG. 4, ZIKALIVax is not cytopathic contrary to what is observed with the epidemic and endemic stains of the virus. The results were confirmed in a LDH release assay. Briefly, Vero cells were infected with the different clones at MOI of 0.1 PFU/cell and LDH activity in cell supernatants was determined using a colorimetric LDH quantification assay kit. The results are depicted in FIG. 5.

Then the production of the different clones were then determined in a plaque forming assay. Briefly, Vero cells ($10^e5$/well) were seeded in 48-well culture plates. Tenfold serial dilutions of virus samples were prepared in duplicate in culture medium supplemented with 5% heat-inactivated FBS and 0.1 mL of each dilution was added to the cells. The plates were incubated for 2 h at 37° C. 0.1 ml of culture medium supplemented with 0.8% carboxymethylcellulose (CMC) was added to each well, followed by an incubation at 37° C. for 4 days. The CMC overlay was removed and the cells were first fixed with 3.7% PFA for 10 min and then stained with 0.5% crystal violet in 20% ethanol. Plaques were counted and expressed as plaque-forming units per mL (PFU·mL$^{-1}$). As shown in Table 1, the progeny production of ZIKALIVax is significantly increased in comparison to the production observed with the epidemic and endemic virus. FIG. 6 shows the progeny virus infection in Vero cells infected with ZIKV clones A to F.

TABLE 1

Progeny ZIKV production on Vero cells (passage 2) (log PFU · mL$^{-1}$) of the different clones.

| Clone | Progeny ZIKV production on Vero cells (passage 2) (log PFU · mL$^{-1}$) |
| --- | --- |
| A | 7.0 |
| B | 7.5 |
| C | 8.0 |
| D | 6.0 |
| E | 5.0 |
| F | 8.3 |

In conclusion, the ZIKALIVax can be produced at very high level without being cytopathic. Moreover, the absence of N-glycosylation will prevent the generation of autoantibodies responsible for Guillain-Barré syndrome. This clone thus represents a very good candidate for the production of an attenuated vaccine.

SEQUENCES

E glycoprotein from ZIKV strain BeH 819015 (Genbank #access KU365778.1)

SEQ ID NO: 1

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

The E sequences of mutant [E-I152T, E-T156I, E-H158Y] of ZIKVBR15-MC

SEQ ID NO: 2

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

-continued

WGNGCGLFGKGSLVTCAKFACSKKMTGKSIQPENLEYRIMLSVHGSQHSG

MTVNDIGYETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSGSTIGKAFEATVRGAKRMAVLGDTAWDFGSVGGALNSLGKGIHQIFG

AAFKSLFGGMSWFSQILIGTLLMWLGLNTKNGSISLMCLALGGVLIFLST

AVSA

Polyprotein sequence of chimeric ZIKVBR15-
MC mutant
[E-I152T, E-T156I, E-H158Y] (3,423 aa)

SEQ ID NO: 3

MKNPKKKSGGFRIVNMLKRGVARVSPFGGLKRLPAGLLLGHGPIRMVLAI

LAFLRFTAIKPSLGLINRWGSVGKKEAMEIIKKFKKDLAAMLRIINARKE

KKRRGADTSVGIVGLLLTTAMAAEVTRRGSAYYMYLDRNDAGEAISFPTT

LGMNKCYIQIMDLGHMCDATMSYECPMLDEGVEPDDVDCWCNTTSTWVVY

GTCHHKKGEARRSRRAVTLPSHSTRKLQTRSQTWLESREYTKHLIRVENW

IFRNPGFALAAAAIAWLLGSSTSQKVIYLVMILLIAPAYSIRCIGVSNRD

FVEGMSGGTWVDVVLEHGGCVTVMAQDKPTVDIELVTTTVSNMAEVRSYC

YEASISDMASDSRCPTQGEAYLDKQSDTQYVCKRTLVDRGWGNGCGLFGK

GSLVTCAKFACSKKMTGKSIQPENLEYRIMLSVHGSQHSGMTVNDIGYET

DENRAKVEITPNSPRAEATLGGFGSLGLDCEPRTGLDFSDLYYLTMNNKH

WLVHKEWFHDIPLPWHAGADTGTPHWNNKEALVEFKDAHAKRQTVVVLGS

QEGAVHTALAGALEAEMDGAKGRLSSGHLKCRLKMDKLRLKGVSYSLCTA

AFTFTKIPAETLHGTVTVEVQYAGTDGPCKVPAQMAVDMQTLTPVGRLIT

ANPVITESTENSKMMLELDPPFGDSYIVIGVGEKKITHHWHRSGSTIGKA

FEATVRGAKRMAVLGDTAWDFGSVGGALNSLGKGIHQIFGAAFKSLFGGM

SWFSQILIGTLLMWLGLNTKNGSISLMCLALGGVLIFLSTAVSADVGCSV

DFSKKETRCGTGVFVYNDVEAWRDRYKYHPDSPRRLAAAVKQAWEDGICG

ISSVSRMENIMWRSVEGELNAILEENGVQLTVVVGSVKNPMWRGPQRLPV

PVNELPHGWKAWGKSYFVRAAKTNNSFVVDGDTLKECPLKHRAWNSFLVE

DHGFGVFHTSVWLKVREDYSLECDPAVIGTAVKGKEAVHSDLGYWIESEK

NDTWRLKRAHLIEMKTCEWPKSHTLWTDGIEESDLIIPKSLAGPLSHHNT

REGYRTQMKGPWHSEELEIRFEECPGTKVHVEETCGTRGPSLRSTTASGR

VIEEWCCRECTMPPLSFRAKDGCWYGMEIRPRKEPESNLVRSMVTAGSTD

HMDHFSLGVLVILLMVQEGLKKRMTTKIIISTSMAVLVAMILGGFSMSDL

AKLAILMGATFAEMNTGGDVAHLALIAAFKVRPALLVSFIFRANWTPRES

MLLALASCLLQTAISALEGDLMVLINGFALAWLAIRAMVVPRTDNITLAI

LAALTPLARGTLLVAWRAGLATCGGFMLLSLKGKGSVKKNLPFVMALGLT

AVRLVDPINVVGLLLLTRSGKRSWPPSEVLTAVGLICALAGGFAKADIEM

AGPMAAVGLLIVSYVVSGKSVDMYIERAGDITWEKDAEVTGNSPRLDVAL

DESGDFSLVEDDGPPMREIILKVVLMTICGMNPIAIPFAAGAWYVYVKTG

KRSGALWDVPAPKEVKKGETTDGVYRVMTRRLLGSTQVGVGVMQEGVFHT

MWHVTKGSALRSGEGRLDPYWGDVKQDLVSYCGPWKLDAAWDGHSEVQLL

AVPPGERARNIQTLPGIFKTKDGDIGAVALDYPAGTSGSPILDKCGRVIG

LYGNGVVIKNGSYVSAITQGRREEETPVECFEPSMLKKKQLTVLDLHPGA

GKTRRVLPEIVREAIKTRLRTVILAPTRVVAAEMEEALRGLPVRYMTTAV

NVTHSGTEIVDLMCHATFTSRLLQPIRVPNYNLYIMDEAHFTDPSSIAAR

GYISTRVEMGEAAAIFMTATPPGTRDAFPDSNSPIMDTEVEVPERAWSSG

FDWVTDHSGKTVWFVPSVRNGNEIAACLTKAGKRVIQLSRKTFETEFQKT

KHQEWDFVVTTDISEMGANFKADRVIDSRRCLKPVILDGERVILAGPMPV

THASAAQRRGRIGRNPNKPGDEYLYGGGCAETDEDHAHWLEARMLLDNIY

LQDGLIASLYRPEADKVAAIEGEFKLRTEQRKTFVELMKRGDLPVWLAYQ

VASAGITYTDRRWCFDGTTNNTIMEDSVPAEVWTRHGEKRVLKPRWMDAR

VCSDHAALKSFKEFAAGKRGAAFGVMEALGTLPGHMTERFQEAIDNLAVL

MRAETGSRPYKAAAAQLPETLETIMLLGLLGTVSLGIFFVLMRNKGIGKM

GFGMVTLGASAWLMWLSEIEPARIACVLIVVFLLLVVLIPEPEKQRSPQD

NQMAIIIMVAVGLLGLITANELGWLERTKSDLSHLMGRREEGATIGFSMD

IDLRPASAWAIYAALTTFITPAVQHAVTTSYNNYSLMAMATQAGVLFGMG

KGMPFYAWDFGVPLLMIGCYSQLTPLTLIVAIILLVAHYMYLIPGLQAAA

ARAAQKRTAAGIMKNPVVDGIVVTDIDTMTIDPQVEKKMGQVLLIAVAVS

SAILSRTAWGWGEAGALITAATSTLWEGSPNKYWNSSTATSLCNIFRGSY

LAGASLIYTVTRNAGLVKRRGGGTGETLGEKWKARLNQMSALEFYSYKKS

GITEVCREEARRALKDGVATGGHAVSRGSAKLRWLVERGYLQPYGKVIDL

GCGRGGWSYYAATIRKVQEVKGYTKGGPGHEEPVLVQSYGWNIVRLKSGV

DVFHMAAEPCDTLLCDIGESSSSPEVEEARTLRVLSMVGDWLEKRPGAFC

IKVLCPYTSTMMETLERLQRRYGGGLVRVPLSRNSTHEMYWVSGAKSNTI

KSVSTTSQLLLGRMDGPRRPVKYEEDVNLGSGTRAVVSCAEAPNMKIIGN

RIERIRSEHAETWFFDENHPYRTWAYHGSYEAPTQGSASSLINGVVRLLS

KPWDVVTGVTGIAMTDTTPYGQQRVFKEKVDTRVPDPQEGTRQVMSMVSS

WLWKELGKHKRPRVCTKEEFINKVRSNAALGAIFEEEKEWKTAVEAVNDP

RFWALVDKEREHHLRGECQSCVYNMMGKREKKQGEFGKAKGSRAIWYMWL

GARFLEFEALGFLNEDHWMGRENSGGGVEGLGLQRLGYVLEEMSRIPGGR

MYADDTAGWDTRISRFDLENEALITNQMEKGHRALALAIIKYTYQNKVVK

VLRPAEKGKTVMDIISRQDQRGSGQVVTYALNTFTNLVVQLIRNMEAEEV

LEMQDLWLLRRSEKVTNWLQSNGWDRLKRMAVSGDDCVVKPIDDRFAHAL

RFLNDMGKVRKDTQEWKPSTGWDNWEEVPFCSHHFNKLHLKDGRSIVVPC

RHQDELIGRARVSPGAGWSIRETACLAKSYAQMWQLLYFHRRDLRLMANA

ICSSVPVDWVPTGRTTWSIHGKGEWMTTEDMLVVWNRVWIEENDHMEDKT

PVTKWTDIPYLGKREDLWCGSLIGHRPRTTWAENIKNTVNMVRRIIGDEE

KYMDYLSTQVRYLGEEGSTPGVL*

-continued

Genomic sequence of chimeric ZIKVBR15-MC mutant
[E-I152T, E-T156I, E-H158Y] (10,807 nt)

SEQ ID NO: 4

AGTTGTTGATCTGTGTGAGTCAGACTGCGACAGTTCGAGTCTGAAGCGAG
AGCTAACAACAGTATCAACAGGTTTAATTTGGATTTGGAAACGAGAGTTT
CTGGTCATGAAAAACCCAAAAAAGAAATCCGGAGGATTCCGGATTGTCAA
TATGCTAAAACGCGGAGTAGCCCGTGTGAGCCCCTTTGGGGGCTTGAAGA
GGCTGCCAGCCGGACTTCTGCTGGGTCATGGGCCCATCAGGATGGTCTTG
GCGATTCTAGCCTTTTTGAGATTCACGGCAATCAAGCCATCACTGGGTCT
CATCAATAGATGGGGTTCAGTTGGGAAAAAGAGGCTATGGAAATAATAA
AGAAGTTCAAGAAAGATCTGGCTGCCATGCTGAGAATAATCAATGCTAGG
AAGGAGAAGAAGAGACGAGGCGCAGATACTAGTGTCGGAATTGTTGGCCT
CCTGCTGACCACAGCTATGGCAGCGGAGGTCACTAGACGTGGGAGTGCAT
ACTATATGTACTTGGACAGAAACGATGCTGGGGAGGCCATATCTTTTCCA
ACCACATTGGGGATGAATAAGTGTTATATACAGATCATGGATCTTGGACA
CATGTGTGATGCCACCATGAGCTATGAATGCCCTATGCTGGATGAGGGGG
TGGAACCAGATGACGTCGATTGTTGGTGCAACACGACGTCAACTTGGGTT
GTGTACGGAACCTGCCATCACAAAAAAGGTGAAGCACGGAGATCTAGAAG
AGCTGTGACGCTCCCCTCCCATTCCACTAGGAAGCTGCAAACGCGGTCGC
AAACCTGGTTGAATCAAGAGAATACACAAAGCACTTGATTAGAGTCGAA
AATTGGATATTCAGGAACCCTGGCTTCGCGTTAGCAGCAGCTGCCATCGC
TTGGCTTTTGGGAAGCTCAACGAGCCAAAAAGTCATATACTTGGTCATGA
TACTGCTGATTGCCCCGGCATACAGCATCAGGTGCATAGGAGTCAGCAAT
AGGGACTTTGTGGAAGGTATGTCAGGTGGGACTTGGGTTGATGTTGTCTT
GGAACATGGAGGTTGTGTCACCGTAATGGCACAGGACAAACCGACTGTCG
ACATAGAGCTGGTTACAACAACAGTCAGCAACATGGCGGAGGTACGATCG
TACTGCTATGAGGCATCAATATCAGACATGGCTTCGGACAGCCGCTGCCC
AACACAAGGTGAAGCCTACCTTGACAAGCAATCAGACACTCAATATGTCT
GCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAAT
GACCGGGAAGAGCATCCAGCCAGAGAATCTGGAGTACCGGATAATGCTGT
CAGTTCATGGCTCCCAGCACAGTGGGATGACTGTCAATGATATAGGATAT
GAAACTGATGAGAATAGAGCGAAAGTTGAGATAACGCCCAATTCACCAAG
AGCCGAAGCCACCCTGGGGGGTTTTGGAAGCCTAGGACTTGATTGTGAAC
CGAGGACAGGCCTTGACTTTTCAGATTTGTATTACTTGACTATGAATAAC
AAGCACTGGTTGGTTCACAAGGAGTGGTTCCACGACATTCCATTACCTTG
GCACGCTGGGGCAGACACCGGAACTCCACACTGGAACAACAAAGAAGCAC
TGGTAGAGTTCAAGGACGCACATGCCAAAAGGCAAACTGTCGTGGTTCTA
GGGAGTCAAGAAGGAGCAGTTCACACGGCCCTTGCTGGAGCTCTGGAGGC
TGAGATGGATGGTGCAAAGGGAAGGCTGTCCTCTGGCCACTTGAAATGTC
GCCTGAAAATGGATAAACTTAGATTGAAGGGCGTGTCATACTCCTTGTGT
ACTGCAGCGTTCACATTCACCAAGATCCCGGCTGAAACACTGCACGGGAC

-continued

AGTCACAGTGGAGGTACAGTACGCAGGGACAGATGGACCTTGCAAGGTTC
CAGCTCAGATGGCGGTGGACATGCAAACTCTGACCCCAGTTGGGAGGTTG
ATAACCGCTAACCCCGTAATCACTGAAAGCACTGAGAACTCTAAGATGAT
GCTGGAACTTGATCCACCATTTGGGGACTCTTACATTGTCATAGGAGTCG
GGGAGAAGAAGATCACCCACCACTGGCACAGGAGTGGCAGCACCATTGGA
AAAGCATTTGAGGCCACTGTGAGAGGCGCCAAGAGAATGGCAGTCCTGGG
GGACACAGCCTGGGACTTTGGATCAGTTGGAGGCGCTCTCAACTCATTGG
GCAAGGGCATCCATCAAATTTTTGGAGCAGCTTTCAAATCATTGTTTGGA
GGAATGTCCTGGTTCTCACAAATTCTCATTGGAACGTTGCTGATGTGGTT
GGGTCTGAACACAAAGAATGGATCTATTTCCCTTATGTGCTTGGCCTTAG
GGGGGGTGTTGATCTTCTTATCCACAGCCGTCTCTGCTGATGTGGGGTGC
TCGGTGGACTTCTCAAAGAAGGAGACGAGATGCGGTACAGGGGTGTTCGT
CTATAACGACGTTGAAGCCTGGAGGGACAGGTACAAGTACCATCCTGACT
CCCCCCGTAGATTGGCAGCAGCAGTCAAGCAAGCCTGGGAAGATGGTATC
TGCGGGATCTCCTCTGTTTCAAGAATGGAAAACATCATGTGGAGATCAGT
AGAAGGGGAGCTCAACGCAATCCTGGAAGAGAATGGAGTTCAACTGACGG
TCGTTGTGGGATCTGTAAAAAACCCCATGTGGAGAGGTCCACAGAGATTG
CCCGTGCCTGTGAACGAGCTGCCCCACGGCTGGAAGGCTTGGGGGAAATC
GTACTTCGTCAGAGCAGCAAAGACAAATAACAGCTTTGTCGTGGATGGTG
ACACACTGAAGGAATGCCCACTCAAACATAGAGCATGGAACAGCTTTCTT
GTGGAGGATCATGGGTTCGGGGTATTTCACACTAGTGTCTGGCTCAAGGT
TAGAGAAGATTATTCATTAGAGTGTGATCCAGCCGTTATTGGAACAGCTG
TTAAGGGAAAGGAGGCTGTACACAGTGATCTAGGCTACTGGATTGAGAGT
GAGAAGAATGACACATGGAGGCTGAAGAGGGCCCATCTGATCGAGATGAA
AACATGTGAATGGCCAAAGTCCCACACATTGTGGACAGATGGAATAGAAG
AGAGTGATCTGATCATACCCAAGTCTTTAGCTGGGCCACTCAGCCATCAC
AATACCAGAGAGGGCTACAGGACCCAAATGAAAGGGCCATGGCACAGTGA
AGAGCTTGAAATTCGGTTTGAGGAATGCCCAGGCACTAAGGTCCACGTGG
AGGAAACATGTGGAACAAGAGGACCATCTCTGAGATCAACCACTGCAAGC
GGAAGGGTGATCGAGGAATGGTGCTGCAGGGAGTGCACAATGCCCCCACT
GTCGTTCCGGGCTAAAGATGGCTGTTGGTATGGAATGGAGATAAGGCCCA
GGAAAGAACCAGAAAGCAACTTAGTAAGGTCAATGGTGACTGCAGGATCA
ACTGATCACATGGACCACTTCTCCCTTGGAGTGCTTGTGATCCTGCTCAT
GGTGCAGGAAGGGCTGAAGAAGAGAATGACCACAAAGATCATCATAAGCA
CATCAATGGCAGTGCTGGTAGCTATGATCCTGGGAGGATTTTCAATGAGT
GACCTGGCTAAGCTTGCAATTTTGATGGGTGCCACCTTCGCGGAAATGAA
CACTGGAGGAGATGTAGCTCATCTGGCGCTGATAGCGGCATTCAAAGTCA
GACCAGCGTTGCTGGTATCTTTCATCTTCAGAGCTAATTGGACACCCCGT
GAAAGCATGCTGCTGGCCTTGGCCTCGTGTCTTTTGCAAACTGCGATCTC
CGCCTTGGAAGGCGACCTGATGGTTCTCATCAATGGTTTGCTTTGGCCT
GGTTGGCAATACGAGCGATGGTTGTTCCACGCACTGATAACATCACCTTG

```
GCAATCCTGGCTGCTCTGACACCACTGGCCCGGGGCACACTGCTTGTGC
GTGGAGAGCAGGCCTTGCTACTTGCGGGGGGTTTATGCTCCTCTCTCTGA
AGGGAAAAGGCAGTGTGAAGAAGAACTTACCATTTGTCATGGCCCTGGGA
CTAACCGCTGTGAGGCTGGTCGACCCCATCAACGTGGTGGGACTGCTGTT
ACTCACAAGGAGTGGGAAGCGGAGCTGGCCCCCTAGCGAAGTACTCACAG
CTGTTGGCCTGATATGCGCATTGGCTGGAGGGTTCGCCAAGGCAGATATA
GAGATGGCTGGGCCCATGGCCGCGGTCGGTCTGCTAATTGTCAGTTACGT
GGTCTCAGGAAAGAGTGTGGACATGTACATTGAAAGAGCAGGTGACATCA
CATGGGAAAAAGATGCGGAAGTCACTGGAAACAGTCCCCGGCTCGATGTG
GCGCTAGATGAGAGTGGTGATTTCTCCCTGGTGGAGGATGACGGTCCCCC
CATGAGAGAGATCATACTCAAGGTGGTCCTGATGACCATCTGTGGCATGA
ATCCAATAGCCATACCCTTTGCAGCTGGAGCGTGGTACGTATACGTGAAG
ACTGGAAAAAGGAGTGGTGCTCTATGGGATGTGCCTGCTCCCAAGGAAGT
AAAAAAGGGGGAGACCACAGATGGAGTGTACAGAGTAATGACTCGTAGAC
TGCTAGGTTCAACACAAGTTGGAGTGGGAGTTATGCAAGAGGGGGTCTTT
CACACTATGTGGCACGTCACAAAAGGATCCGCGCTGAGAAGCGGTGAAGG
GAGACTTGATCCATACTGGGGAGATGTCAAGCAGGATCTGGTGTCATACT
GTGGTCCATGGAAGCTAGATGCCGCCTGGGACGGGCACAGCGAGGTGCAG
CTCTTGGCCGTGCCCCCCGGAGAGAGAGCGAGGAACATCCAGACTCTGCC
CGGAATATTTAAGACAAAGGATGGGGACATTGGAGCGGTTGCGCTGGATT
ACCCAGCAGGAACTTCAGGATCTCCAATCCTAGACAAGTGTGGGAGAGTG
ATAGGACTTTATGGCAATGGGGTCGTGATCAAAAATGGGAGTTATGTTAG
TGCCATCACCCAAGGGAGGAGGGAAGAAGAGACTCCTGTTGAGTGCTTCG
AGCCCTCGATGCTGAAGAAGAAGCAGCTAACTGTCTTAGACTTGCATCCT
GGAGCTGGGAAAACCAGGAGAGTTCTTCCTGAAATAGTCCGTGAAGCCAT
AAAAACAAGACTCCGTACTGTGATCTTAGCTCCAACCAGGGTTGTCGCTG
CTGAAATGGAGGAGGCCCTTAGAGGGCTTCCAGTGCGTTATATGACAACA
GCAGTCAATGTCACCCACTCTGGAACAGAAATCGTCGACTTAATGTGCCA
TGCCACCTTCACTTCACGTCTACTACAGCCAATCAGAGTCCCCAACTATA
ATCTGTATATTATGGATGAGGCCCACTTCACAGATCCCTCAAGTATAGCA
GCAAGAGGATACATTTCAACAAGGGTTGAGATGGGCGAGGCGGCTGCCAT
CTTCATGACCGCCACGCCACCAGGAACCCGTGACGCATTTCCGGACTCCA
ACTCACCAATTATGGACACCGAAGTGGAAGTCCCAGAGAGAGCCTGGAGC
TCAGGCTTTGATTGGGTGACGGATCATTCTGGAAAAACAGTTTGGTTTGT
TCCAAGCGTGAGGAACGGCAATGATCGCAGCTTGTCTGACAAAGGCTG
GAAAACGGGTCATACAGCTCAGCAGAAAGACTTTTGAGACAGAGTTCCAG
AAAACAAAACATCAAGAGTGGGACTTTGTCGTGACAACTGACATTTCAGA
GATGGGCGCCAACTTTAAAGCTGACCGTGTCATAGATTCCAGGAGATGCC
TAAAGCCGGTCATACTTGATGGCGAGAGAGTCATTCTGGCTGGACCCATG
CCTGTCACACATGCCAGCGCTGCCCAGAGGAGGGGGCGCATAGGCAGGAA
TCCCAACAAACCTGGAGATGAGTATCTGTATGGAGGTGGGTGCGCAGAGA
CTGACGAAGACCATGCACACTGGCTTGAAGCAAGAATGCTCCTTGACAAT
ATTTACCTCCAAGATGGCCTCATAGCCTCGCTCTATCGACCTGAGGCCGA
CAAAGTAGCAGCCATTGAGGGAGAGTTCAAGCTTAGGACGGAGCAAAGGA
AGACCTTTGTGGAACTCATGAAAAGAGGAGATCTTCCTGTTTGGCTGGCC
TATCAGGTTGCATCTGCCGGAATAACCTACACAGATAGAAGATGGTGCTT
TGATGGCACGACCAACAACACCATAATGGAAGATAGTGTGCCGGCAGAGG
TGTGGACCAGACACGGAGAGAAAAGAGTGCTCAAACCGAGGTGGATGGAC
GCCAGAGTTTGTTCAGATCATGCGGCCCTGAAGTCATTCAAGGAGTTTGC
CGCTGGGAAAAGAGGAGCGGCTTTTGGAGTGATGGAAGCCCTGGGAACAC
TGCCAGGACACATGACAGAGAGATTCCAGGAAGCCATTGACAACCTCGCT
GTGCTCATGCGGGCAGAGACTGGAAGCAGGCCTTACAAAGCCGCGGCGGC
CCAATTGCCGGAGACCCTAGAGACCATAATGCTTTTGGGGTTGCTGGGAA
CAGTCTCGCTGGGAATCTTCTTCGTCTTGATGAGGAACAAGGGCATAGGG
AAGATGGGCTTTGGAATGGTGACTCTTGGGGCCAGCGCATGGCTCATGTG
GCTCTCGGAAATTGAGCCAGCCAGAATTGCATGTGTCCTCATTGTTGTGT
TCCTATTGCTGGTGGTGCTCATACCTGAGCCAGAAAAGCAAAGATCTCCC
CAGGACAACCAAATGGCAATCATCATCATGGTAGCAGTAGGTCTTCTGGG
CTTGATTACCGCCAATGAACTCGGATGGTTGGAGAGAACAAAGAGTGACC
TAAGCCATCTAATGGGAAGGAGAGAGGAGGGGGCAACCATAGGATTCTCA
ATGGACATTGACCTGCGGCCAGCCTCAGCTTGGGCCATCTATGCTGCCTT
GACAACTTTCATTACCCCAGCCGTCCAACATGCAGTGACCACTTCATACA
ACAACTACTCCTTAATGGCGATGGCCACGCAAGCTGGAGTGTTGTTTGGT
ATGGGCAAAGGGATGCCATTCTACGCATGGGACTTTGGAGTCCCGCTGCT
AATGATAGGTTGCTACTCACAATTAACACCCCTGACCCTAATAGTGGCCA
TCATTTTGCTCGTGGCGCACTACATGTACTTGATCCCAGGGCTGCAGGCA
GCAGCTGCGCGTGCTGCCCAGAAGAGAACGGCAGCTGGCATCATGAAGAA
CCCTGTTGTGGATGGAATAGTGGTGACTGACATTGACACAATGACAATTG
ACCCCCAAGTGGAGAAAAAGATGGGACAGGTGCTACTCATAGCAGTAGCC
GTCTCCAGCGCCATACTGTCGCGGACCGCCTGGGGGTGGGGGAGGCTGG
GGCCCTGATCACAGCCGCAACTTCCACTTTGTGGGAAGGCTCTCCGAACA
AGTACTGGAACTCCTCTACAGCCACTTCACTGTGTAACATTTTTAGGGGA
AGTTACTTGGCTGGAGCTTCTCTAATCTACACAGTAACAAGAAACGCTGG
CTTGGTCAAGAGACGTGGGGGTGGAACAGGAGAGACCCTGGGAGAGAAAT
GGAAGGCCCGCTTGAACCAGATGTCGGCCCTGGAGTTCTACTCCTACAAA
AAGTCAGGCATCACCGAGGTGTGCAGAGAAGAGGCCCGCCGCGCCCTCAA
GGACGGTGTGGCAACGGGAGGCCATGCTGTGTCCCGAGGAAGTGCAAAGC
TGAGATGGTTGGTGGAGCGGGATACCTGCAGCCCTATGGAAAGGTCATT
GATCTTGGATGTGGCAGAGGGGCTGGAGTTACTACGCCGCCACCATCCG
CAAAGTTCAAGAAGTGAAAGGATACACAAAAGGAGGCCCTGGTCATGAAG
AACCCGTGTTGGTGCAAAGCTATGGGTGGAACATAGTCCGTCTTAAGAGT
```

-continued

```
GGGGTGGACGTCTTTCATATGGCGGCTGAGCCGTGTGACACGCTGCTGTG
TGACATAGGTGAGTCATCATCAGTCCTGAAGTGGAAGAAGCACGGACGC
TCAGAGTCCTCTCCATGGTGGGGGATTGGCTTGAAAAAAGACCAGGAGCC
TTTTGTATAAAAGTGTTGTGCCCATACACCAGCACTATGATGGAAACCCT
GGAGCGACTGCAGCGTAGGTATGGGGGAGGACTGGTCAGAGTGCCACTCT
CCCGCAACTCTACACATGAGATGTACTGGGTCTCTGGAGCGAAAAGCAAC
ACCATAAAAGTGTGTCCACCACGAGCCAGCTCCTCTTGGGGCGCATGGA
CGGGCCTAGGAGGCCAGTGAAATATGAGGAGGATGTGAATCTCGGCTCTG
GCACGCGGGCTGTGGTAAGCTGCGCTGAAGCTCCCAACATGAAGATCATT
GGTAACCGCATTGAAAGGATCCGCAGTGAGCACGCGGAAACGTGGTTCTT
TGACGAGAACCACCCATATAGGACATGGCTTACCATGGAAGCTATGAGG
CCCCCACACAAGGGTCAGCGTCCTCTCTAATAAACGGGGTTGTCAGGCTC
CTGTCAAAACCCTGGGATGTGGTGACTGGAGTCACAGGAATAGCCATGAC
CGACACCACACCGTATGGTCAGCAAAGAGTTTTCAAGGAAAAAGTGGACA
CTAGGGTGCCAGACCCCCAAGAAGGCACTCGTCAGGTTATGAGCATGGTC
TCTTCCTGGTTGTGGAAAGAGCTAGGCAAACACAAACGGCCACGAGTCTG
TACCAAAGAAGAGTTCATCAACAAGGTTCGTAGCAATGCAGCATTAGGGG
CAATATTTGAAGAGGAAAAAGAGTGGAAGACTGCAGTGGAAGCTGTGAAC
GATCCAAGGTTCTGGGCTCTAGTGGACAAGGAAAGAGAGCACCACCTGAG
AGGAGAGTGCCAGAGTTGTGTGTATAACATGATGGGAAAAGAGAAAAGA
AACAAGGGGAATTTGGAAAGGCCAAGGGCAGCCGCGCCATCTGGTATATG
TGGCTAGGGGCTAGATTCTAGAGTTCGAAGCCCTTGGATTCTTGAACGA
GGATCACTGGATGGGGAGAGAGAACTCAGGAGGTGGTGTTGAAGGGCTGG
GATTACAAAGACTCGGATATGTCCTAGAAGAGATGAGTCGTATACCAGGA
GGAAGGATGTATGCAGATGACACTGCTGGCTGGGACACCCGCATTAGCAG
GTTTGATCTGGAGAATGAAGCTCTAATCACCAACCAAATGGAGAAAGGGC
ACAGGGCCTTGGCATTGGCCATAATCAAGTACACATACCAAAACAAAGTG
GTAAAGGTCCTTAGACCAGCTGAAAAAGGGAAAACAGTTATGGACATTAT
TTCGAGACAAGACCAAAGGGGGAGCGGACAAGTTGTCACTTACGCTCTTA
ACACATTTACCAACCTAGTGGTCAACTCATTCGGAATATGGAGGCTGAG
GAAGTTCTAGAGATGCAAGACTTGTGGCTGCTGCGGAGGTCAGAGAAAGT
GACCAACTGGTTGCAGAGCAACGGATGGGATAGGCTCAAACGAATGGCAG
TCAGTGGAGATGATTGCGTTGTGAAGCCAATTGATGATAGGTTTGCACAT
GCCCTCAGGTTCTTGAATGATATGGGAAAAGTTAGAAAGGACACACAAGA
GTGGAAACCCTCAACTGGATGGACAACTGGGAAGAAGTTCCGTTTTGCT
CCCACCACTTCAACAAGCTCCATCTCAAGGACGGGAGGTCCATTGTGGTT
CCCTGCCGCCACCAAGATGAACTGATTGGCCGGGCCCGCGTCTCTCCAGG
GGCGGGATGGAGCATCCGGGAGACTGCTTGCCTAGCAAAATCATATGCGC
AGATGTGGCAGCTCCTTTATTTCCACAGAAGGGACCTCCGACTGATGGCC
AATGCCATTTGTTCATCTGTGCCAGTTGACTGGGTTCCAACTGGGAGAAC
TACCTGGTCAATCCATGGAAAGGGAGAATGGATGACCACTGAAGACATGC
TTGTGGTGTGGAACAGAGTGTGGATTGAGGAGAACGACCACATGGAAGAC
AAGACCCCAGTTACGAAATGGACAGACATTCCCTATTTGGGAAAAAGGGA
AGACTTGTGGTGTGGATCTCTCATAGGGCACAGACCGCGCACCACCTGGG
CTGAGAACATTAAAAACACAGTCAACATGGTGCGCAGGATCATAGGTGAT
GAAGAAAGTACATGGACTACCTATCCACCCAAGTTCGCTACTTGGGTGA
AGAAGGGTCTACACCTGGAGTGCTGTAAGCACCAATTTTAGTGTTGTCAG
GCCTGCTAGTCAGCCACAGTTTGGGGAAAGCTGTGCAGCCTGTAACCCCC
CCAGGAGAAGCTGGGAAACCAAGCTCATAGTCAGGCCGAGAACGCCATGG
CACGGAAGAAGCCATGCTGCCTGTGAGCCCCTCAGAGGACACTGAGTCAA
AAAACCCCACGCGCTTGGAAGCGCAGGATGGGAAAGAAGGTGGCGACCT
TCCCCACCCTTCAATCTGGGGCCTGAACTGGAGACTAGCTGTGAATCTCC
AGCAGAGGGACTAGTGGTTAGAGGAGACCCCCCGGAAAACGCAAAACAGC
ATATTGACGCTGGGAAAGACCAGAGACTCCATGAGTTTCCACCACGCTGG
CCGCCAGGCACAGATCGCCGAACAGCGGCGGCCGGTGTGGGGAAATCCAT
GGTTTCT
```

Polyprotein sequence the chimeric ZIKALIVax virus (10,807 nt; 3,423 aa)

SEQ ID NO: 5

```
MKNPKKKSGGFRIVNMLKRGVARVSPFGGLKRLPAGLLLGHGPIRMVLAI
LAFLRFTAIKPSLGLINRWGSVGKKEAMEIIKKFKKDLAAMLRIINARKE
KKRRGADTSVGIVGLLLTTAMAAEVTRRGSAYYMYLDRNDAGEAISFPTT
LGMNKCYIQIMDLGHMCDATMSYECPMLDEGVEPDDVDCWCNTTSTWVVY
GTCHHKKGEARRSRRAVTLPSHSTRKLQTRSQTWLESREYTKHLIRVENW
IFRNPGFALAAAAIAWLLGSSTSQKVIYLVMILLIAPAYSIRCIGVSNRD
FVEGMSGGTWVDVVLEHGGCVTVMAQDKPTVDIELVTTTVSNMAEVRSYC
YEASISDMASDSRCPTQGEAYLDKQSDTQYVCKRTLVDRGWGNGCGLFGK
GSLVTCAKFACSKKMTGKSIQPENLEYRIMLSVHGSQHSGMTVNDIGYET
DENRAKVEITPNSPRAEATLGGFGSLGLDCEPRTGLDFSDLYYLTMNNKH
WLVHKEWFHDIPLPWHAGADTGTPHWNNKEALVEFKDAHAKRQTVVVLGS
QEGAVHTALAGALEAEMDGAKGRLSSGHLKCRLKMDKLRLKGVSYSLCTA
AFTFTKIPAETLHGTVTVEVQYAGTDGPCKVPAQMAVDMQTLTPVGRLIT
ANPVITESTENSKMMLELDPPFGDSYIVIGVGEKKITHHWHRSGSTIGKA
FEATVRGAKRMAVLGDTAWDFGSVGGVFNSLGKGIHQIFGAAFKSLFGGM
SWFSQILIGTLLVWLGLNTKNGSISLTCLALGGVMIFLSTAVSADVGCSV
DFSKKETRCGTGVFIYNDVEAWRDRYKYHPDSPRRLAAAVKQAWEEGICG
ISSVSRMENIMWKSVEGELNAILEENGVQLTVVVGSVKNPMWRGPQRLPV
PVNELPHGWKAWGKSYFVRAAKTNNSFVVDGDTLKECPLEHRAWNSFLVE
DHGFGVFHTSVWLKVREDYSLECDPAVIGTAVKGREAAHSDLGYWIESEK
NDTWRLKRAHLIEMKTCEWPKSHTLWTDGVEESDLIIPKSLAGPLSHHNT
REGYRTQVKGPWHSEELEIRFEECPGTKVYVEETCGTRGPSLRSTTASGR
VIEEWCCRECTMPPLSFRAKDGCWYGMEIRPRKEPESNLVRSMVTAGSTD
```

HMDHFSLGVLVILLMVQEGLKKRMTTKIIMSTSMAVLVVMILGGFSMSDL
AKLVILMGATFAEMNTGGDVAHLALVAAFKVRPALLVSFIFRANWTPRES
MLLALASCLLQTAISALEGDLMVLINGFALAWLAIRAMAVPRTDNIALPI
LAALTPLARGTLLVAWRAGLATCGGIMLLSLKGKGSVKKNLPFVMALGLT
AVRVVDPINVVGLLLLTRSGKRSWPPSEVLTAVGLICALAGGFAKADIEM
AGPMAAVGLLIVSYVVSGKSVDMYIERAGDITWEKDAEVTGNSPRLDVAL
DESGDFSLVEEDGPPMREIILKVVLMAICGMNPIAIPFAAGAWYVYVKTG
KRSGALWDVPAPKEVKKGETTDGVYRVMTRRLLGSTQVGVGVMQEGVFHT
MWHVTKGAALRSGEGRLDPYWGDVKQDLVSYCGPWKLDAAWDGLSEVQLL
AVPPGERARNIQTLPGIFKTKDGDIGAVALDYPAGTSGSPILDKCGRVIG
LYGNGVVIKNGSYVSAITQGKREEETPVECFEPSMLKKKQLTVLDLHPGA
GKTRRVLPEIVREAIKKRLRTVILAPTRVVAAEMEEALRGLPVRYMTTAV
NVTHSGTEIVDLMCHATFTSRLLQPIRVPNYNLYIMDEAHFTDPSSIAAR
GYISTRVEMGEAAAIFMTATPPGTRDAFPDSNSPIMDTEVEVPERAWSSG
FDWVTDHSGKTVWFVPSVRNGNEIAACLTKAGKRVIQLSRKTFETEFQKT
KNQEWDFVITTDISEMGANFKADRVIDSRRCLKPVILDGERVILAGPMPV
THASAAQRRGRIGRNPNKPGDEYMYGGGCAETDEGHAHWLEARMLLDNIY
LQDGLIASLYRPEADKVAAIEGEFKLRTEQRKTFVELMKRGDLPVWLAYQ
VASAGITYTDRRWCFDGTTNNTIMEDSVPAEVWTKYGEKRVLKPRWMDAR
VCSDHAALKSFKEFAAGKRGAALGVMEALGTLPGHMTERFQEAIDNLAVL
MRAETGSRPYKAAAAQLPETLETIMLLGLLGTVSLGIFFVLMRNKGIGKM
GFGMVTLGASAWLMWLSEIEPARIACVLIVVFLLLVVLIPEPEKQRSPQD
NQMAIIIMVAVGLLGLITANELGWLERTKNDIAHLMGRREEGATMGFSMD
IDLRPASAWAIYAALTTLITPAVQHAVTTSYNNYSLMAMATQAGVLFGMG
KGMPFYAWDLGVPLLMMGCYSQLTPLTLIVAIILLVAHYMYLIPGLQAAA
ARAAQKRTAAGIMKNPVVDGIVVTDIDTMTIDPQVEKKMGQVLLIAVAIS
SAVLLRTAWGWGEAGALITAATSTLWEGSPNKYWNSSTATSLCNIFRGSY
LAGASLIYTVTRNAGLVKRRGGGTGETLGEKWKARLNQMSALEFYSYKKS
GITEVCREEARRALKDGVATGGHAVSRGSAKLRWLVERGYLQPYGKVVDL
GCGRGGWSYYAATIRKVQEVRGYTKGGPGHEEPMLVQSYGWNIVRLKSGV
DVFHMAAEPCDTLLCDIGESSSSPEVEETRTLRVLSMVGDWLEKRPGAFC
IKVLCPYTSTMMETMERLQRRHGGGLVRVPLSRNSTHEMYWVSGAKSNII
KSVSTTSQLLLGRMDGPRRPVKYEEDVNLGSGTRAVASCAEAPNMKIIGR
RIERIRNEHAETWFLDENHPYRTWAYHGSYEAPTQGSASSLVNGVVRLLS
KPWDVVTGVTGIAMTDTTPYGQQRVFKEKVDTRVPDPQEGTRQVMNIVSS
WLWKELGKRKRPRVCTKEEFINKVRSNAALGAIFEEEKEWKTAVEAVNDP
RFWALVDRERHHLRGECHSCVYNMMGKREKKQGEFGKAKGSRAIWYMWL
GARFLEFEALGFLNEDHWMGRENSGGGVEGLGLQRLGYILEEMNRAPGGK
MYADDTAGWDTRISKFDLENEALITNOMEEGHRTLALAVIKYTYQNKVVK
VLRPAEGGKTVMDIISRQDORGSGOVVTYALNTFTNLVVQLIRNMEAEEV
LEMQDLWLLRKPEKVTRWLQSNGWDRLKRMAVSGDDCVVKPIDDRFAHAL

RFLNDMGKVRKDTQEWKPSTGWSNWEEVPFCSHHFNKLYLKDGRSIVVPC
RHODELIGRARVSPGAGWSIRETACLAKSYAQMWQLLYFHRRDLRLMANA
ICSAVPVDWVPTGRTTWSIHGKGEWMTTEDMLMVWNRVWIEENDHMEDKT
PVTKWTDIPYLGKREDLWCGSLIGHRPRTTWAENIKDTVNMVRRIIGDEE
KYMDYLSTQVRYLGEEGSTPGVL

Genomic sequence of the chimeric ZIKALIVax virus
(10,807 nt; 3,423 aa):
SEQ ID NO: 6
AGTTGTTGATCTGTGTGAGTCAGACTGCGACAGTTCGAGTCTGAAGCGAG
AGCTAACAACAGTATCAACAGGTTTAATTTGGATTTGGAAACGAGAGTTT
CTGGTCATGAAAAACCCAAAAAGAAATCCGGAGGATTCCGGATTGTCAA
TATGCTAAAACGCGGAGTAGCCCGTGTGAGCCCCTTTGGGGGCTTGAAGA
GGCTGCCAGCCGGACTTCTGCTGGGTCATGGGCCCATCAGGATGGTCTTG
GCGATTCTAGCCTTTTTGAGATTCACGGCAATCAAGCCATCACTGGGTCT
CATCAATAGATGGGGTTCAGTTGGGAAAAAGAGGCTATGGAAATAATAA
AGAAGTTCAAGAAAGATCTGGCTGCCATGCTGAGAATAATCAATGCTAGG
AAGGAGAAGAAGAGACGAGGCGCAGATACTAGTGTCGGAATTGTTGGCCT
CCTGCTGACCACAGCTATGGCAGCGGAGGTCACTAGACGTGGGAGTGCAT
ACTATATGTACTTGGACAGAAACGATGCTGGGGAGGCCATATCTTTTCCA
ACCACATTGGGGATGAATAAGTGTTATATACAGATCATGGATCTTGGACA
CATGTGTGATGCCACCATGAGCTATGAATGCCCTATGCTGGATGAGGGGG
TGGAACCAGATGACGTCGATTGTTGGTGCAACACGACGTCAACTTGGGTT
GTGTACGGAACCTGCCATCACAAAAAAGGTGAAGCACGGAGATCTAGAAG
AGCTGTGACGCTCCCCTCCCATTCCACTAGGAAGCTGCAAACGCGGTCGC
AAACCTGGTTGGAATCAAGAGAATACACAAAGCACTTGATTAGAGTCGAA
AATTGGATATTCAGGAACCCTGGCTTCGCGTTAGCAGCAGCTGCCATCGC
TTGGCTTTTGGGAAGCTCAACGAGCCAAAAAGTCATATACTTGGTCATGA
TACTGCTGATTGCCCCGGCATACAGCATCAGGTGCATAGGAGTCAGCAAT
AGGGACTTTGTGGAAGGTATGTCAGGTGGGACTTGGGTTGATGTTGTCTT
GGAACATGGAGGTTGTGTCACCGTAATGGCACAGGACAAACCGACTGTCG
ACATAGAGCTGGTTACAACAACAGTCAGCAACATGGCGGAGGTACGATCG
TACTGCTATGAGGCATCAATATCAGACATGGCTTCGGACAGCCGCTGCCC
AACACAAGGTGAAGCCTACCTTGACAAGCAATCAGACACTCAATATGTCT
GCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAAT
GACCGGGAAGAGCATCCAGCCAGAGAATCTGGAGTACCGGATAATGCTGT
CAGTTCATGGCTCCCAGCACAGTGGGATGACTGTCAATGATATAGGATAT
GAAACTGATGAGAATAGAGCGAAAGTTGAGATAACGCCCAATTCACCAAG
AGCCGAAGCCACCCTGGGGGGTTTTGGAAGCCTAGGACTTGATTGTGAAC
CGAGGACAGGCCTTGACTTTTCAGATTTGTATTACTTGACTATGAATAAC
AAGCACTGGTTGGTTCACAAGGAGTGGTTCCACGACATTCCATTACCTTG
GCACGCTGGGGCAGACACCGGAACTCCACACTGGAACAACAAAGAAGCAC -continued

```
TGGTAGAGTTCAAGGACGCACATGCCAAAAGGCAAACTGTCGTGGTTCTA
GGGAGTCAAGAAGGAGCAGTTCACACGGCCCTTGCTGGAGCTCTGGAGGC
TGAGATGGATGGTGCAAAGGGAAGGCTGTCCTCTGGCCACTTGAAATGTC
GCCTGAAAATGGATAAACTTAGATTGAAGGGCGTGTCATACTCCTTGTGT
ACTGCAGCGTTCACATTCACCAAGATCCCGGCTGAAACACTGCACGGGAC
AGTCACAGTGGAGGTACAGTACGCAGGGACAGATGGACCTTGCAAGGTTC
CAGCTCAGATGGCGGTGGACATGCAAACTCTGACCCCAGTTGGGAGGTTG
ATAACCGCTAACCCCGTAATCACTGAAAGCACTGAGAACTCTAAGATGAT
GCTGGAACTTGATCCACCATTTGGGGACTCTTACATTGTCATAGGAGTCG
GGGAGAAGAAGATCACCCACCACTGGCACAGGAGTGGCAGCACCATTGGA
AAAGCATTTGAGGCCACTGTGAGAGGCGCCAAGAGAATGGCAGTCCTGGG
GGATACAGCCTGGGACTTCGGATCAGTCGGGGTGTGTTCAACTCACTGG
GTAAGGGCATTCACCAGATTTTTGGAGCAGCCTTCAAATCACTGTTTGGA
GGAATGTCCTGGTTCTCACAGATCCTCATAGGCACGCTGCTAGTGTGGTT
AGGTTTGAACACAAAGAATGGATCTATCTCCCTCACATGCTTGGCCCTGG
GGGGAGTGATGATCTTCCTCTCCACGGCTGTTTCTGCTGACGTGGGGTGC
TCAGTGGACTTCTCAAAAAAGGAAACGAGATGTGGCACGGGGTATTCAT
CTATAATGATGTTGAAGCCTGGAGGGACCGGTACAAGTACCATCCTGACT
CCCCCCGCAGATTGGCAGCAGCAGTCAAGCAGGCCTGGGAAGAGGGGATC
TGTGGGATCTCATCCGTTTCAAGAATGGAAAACATCATGTGGAAATCAGT
AGAAGGGGAGCTCAATGCTATCCTAGAGGAGAATGGAGTTCAACTGACAG
TTGTTGTGGGATCTGTAAAAAACCCCATGTGGAGAGGTCCACAAAGATTG
CCAGTGCCTGTGAATGAGCTGCCCCATGGCTGGAAAGCCTGGGGGAAATC
GTATTTTGTTAGGGCGGCAAAGACCAACAACAGTTTTGTTGTCGACGGTG
ACACACTGAAGGAATGTCCGCTTGAGCACAGAGCATGGAATAGTTTTCTT
GTGGAGGATCACGGGTTTGGAGTCTTCCACACCAGTGTCTGGCTTAAGGT
CAGAGAAGATTACTCATTAGAATGTGACCCAGCCGTCATAGGAACAGCTG
TTAAGGGAAGGGAGGCCGCGCACAGTGATCTGGGCTATTGGATTGAAAGT
GAAAAGAATGACACATGGAGGCTGAAGAGGGCCCACCTGATTGAGATGAA
AACATGTGAATGGCCAAAGTCTCACACATTGTGGACAGATGGAGTAGAAG
AAAGTGATCTTATCATACCCAAGTCTTTAGCTGGTCCACTCAGCCACCAC
AACACCAGAGAGGGTTACAGAACCCAAGTGAAAGGGCCATGGCACAGTGA
AGAGCTTGAAATCCGGTTTGAGGAATGTCCAGGCACCAAGGTTTACGTGG
AGGAGACATGCGGAACTAGAGGACCATCTCTGAGATCAACTACTGCAAGT
GGAAGGGTCATTGAGGAATGGTGCTGTAGGGAATGCACAATGCCCCCACT
ATCGTTTCGAGCAAAAGACGGCTGCTGGTATGGAATGGAGATAAGGCCCA
GGAAAGAACCAGAGAGCAACTTAGTGAGGTCAATGGTGACAGCGGGGTCA
ACCGATCATATGGACCACTTCTCTCTTGGAGTGCTTGTGATTCTACTCAT
GGTGCAGGAGGGGTTGAAGAAGAGAATGACCACAAAGATCATCATGAGCA
CATCAATGGCAGTGCTGGTAGTCATGATCTTGGGAGGATTTTCAATGAGT
```

-continued

```
GACCTGGCCAAGCTTGTGATCCTGATGGGTGCTACTTTCGCAGAAATGAA
CACTGGAGGAGATGTAGCTCACTTGGCATTGGTAGCGGCATTTAAAGTCA
GACCAGCCTTGCTGGTCTCCTTCATTTTCAGAGCCAATTGGACACCCCGT
GAGAGCATGCTGCTAGCCCTGGCTTCGTGTCTTCTGCAAACTGCGATCTC
TGCTCTTGAAGGTGACTTGATGGTCCTCATTAATGGATTTGCTTTGGCCT
GGTTGGCAATTCGAGCAATGGCCGTGCCACGCACTGACAACATCGCTCTA
CCAATCTTGGCTGCTCTAACACCACTAGCTCGAGGCACACTGCTCGTGGC
ATGGAGAGCGGGCCTGGCTACTTGTGGAGGGATCATGCTCCTCTCCCTGA
AAGGGAAAGGTAGTGTGAAGAAGAACCTGCCATTTGTCATGGCCCTGGGA
TTGACAGCTGTGAGGGTAGTAGACCCTATTAATGTGGTAGGACTACTGTT
ACTCACAAGGAGTGGGAAGCGGAGCTGGCCCCCTAGTGAAGTTCTCACAG
CCGTTGGCCTGATATGTGCACTGGCCGGAGGGTTTGCCAAGGCAGACATT
GAGATGGCTGGACCCATGGCTGCAGTAGGCTTGCTAATTGTCAGCTATGT
GGTCTCGGGAAAGAGTGTGGACATGTACATTGAAAGAGCAGGTGACATCA
CATGGGAAAAGGACGCGGAAGTCACTGGAAACAGTCCTCGGCTTGACGTG
GCACTGGATGAGAGTGGTGATTTCTCCTTGGTAGAGGAAGATGGTCCACC
CATGAGAGAGATCATACTTAAGGTGGTCCTGATGGCCATCTGTGGCATGA
ACCCAATAGCTATACCTTTTGCTGCAGGAGCGTGGTATGTGTATGTGAAG
ACTGGGAAAAGGAGTGGCGCCCTCTGGGACGTGCCTGCTCCCAAAGAAGT
GAAGAAGGAGAGACCACAGATGGAGTGTACAGAGTGATGACTCGCAGAC
TGCTAGGTTCAACACAGGTTGGAGTGGGAGTCATGCAAGAGGGAGTCTTC
CACACCATGTGGCACGTTACAAAAGGAGCCGCACTGAGGAGCGGTGAGGG
AAGACTTGATCCATACTGGGGGGATGTCAAGCAGGACTTGGTGTCATACT
GTGGGCCTTGGAAGTTGGATGCAGCTTGGGATGGACTCAGCGAGGTACAG
CTTTTGGCCGTACCTCCCGGAGAGAGGGCCAGAAACATTCAGACCCTGCC
TGGAATATTCAAGACAAAGGACGGGACATCGGAGCAGTTGCTCTGGACT
ACCCTGCAGGGACCTCAGGATCTCCGATCCTAGACAAATGTGGAAGAGTG
ATAGGACTCTATGGCAATGGGGTTGTGATCAAGAATGGAAGCTATGTTAG
TGCTATAACCCAGGGAAAGAGGGAGGAGGAGACTCCGGTTGAATGTTTCG
AACCCTCGATGCTGAAGAAGAAGCAGCTAACTGTCTTGGATCTGCATCCA
GGAGCCGGAAAAACCAGGAGAGTTCTTCCTGAAATAGTCCGTGAAGCCAT
AAAAAAGAGACTCCGGACAGTGATCTTGGCACCAACTAGGGTTGTCGCTG
CTGAGATGGAGGAGGCCTTGAGAGGACTTCCGGTGCGTTACATGACAACA
GCAGTCAACGTCACCCATTCTGGGACAGAAATCGTTGATTTGATGTGCCA
TGCCACTTTCACTTCACGCTTACTACAACCCATCAGAGTCCCTAATTACA
ATCTCTACATCATGGATGAAGCCCACTTCACAGACCCCTCAAGTATAGCT
GCAAGAGGATATATATCAACAAGGGTTGAAATGGGCGAGGCGGCTGCCAT
TTTTATGACTGCCACACCACCAGGAACCCGTGATGCGTTTCCTGACTCTA
ACTCACCAATCATGGACACAGAAGTGGAAGTCCCAGAGAGAGCCTGGAGC
TCAGGCTTTGATTGGGTGACAGACCATTCTGGGAAAACAGTTTGGTTCGT
TCCAAGCGTGAGAAACGGAAATGAAATCGCAGCCTGTCTGACAAAGGCTG
```

-continued

GAAAGCGGGTCATACAGCTCAGCAGGAAGACTTTTGAGACAGAATTTCAG

AAAACAAAAAATCAAGAGTGGGACTTTGTCATAACAACTGACATCTCAGA

GATGGGCGCCAACTTCAAGGCTGACCGGGTCATAGACTCTAGGAGATGCC

TAAAACCAGTCATACTTGATGGTGAGAGAGTCATCTTGGCTGGGCCCATG

CCTGTCACGCATGCTAGTGCTGCTCAGAGGAGAGGACGTATAGGCAGGAA

CCCTAACAAACCTGGAGATGAGTACATGTATGGAGGTGGGTGTGCAGAGA

CTGATGAAGGCCATGCACACTGGCTTGAAGCAAGAATGCTTCTTGACAAC

ATCTACCTCCAGGATGGCCTCATAGCCTCGCTCTATCGGCCTGAGGCCGA

TAAGGTAGCCGCCATTGAGGGAGAGTTTAAGCTGAGGACAGAGCAAGGA

AGACCTTCGTGGAACTCATGAAGAGGAGACCTTCCCGTCTGGCTAGCC

TATCAGGTTGCATCTGCCGGAATAACTTACACAGACAGAAGATGGTGCTT

TGATGGCACAACCAACAACACCATAATGGAAGACAGCGTACCAGCAGAGG

TGTGGACAAAGTATGGAGAGAAGAGAGTGCTCAAACCGAGATGGATGGAT

GCTAGGGTCTGTTCAGACCATGCGGCCCTGAAGTCGTTCAAAGAATTCGC

CGCTGGAAAAAGAGGAGCGGCTTTGGGAGTAATGGAGGCCCTGGGAACAC

TGCCAGGACACATGACAGAGAGGTTTCAGGAAGCCATTGACAACCTCGCC

GTGCTCATGCGAGCAGAGACTGGAAGCAGGCCTTATAAGGCAGCGGCAGC

CCAACTGCCGGAGACCCTAGAGACCATTATGCTCTTAGGTTTGCTGGGAA

CAGTTTCACTGGGGATCTTCTTCGTCTTGATGCGGAATAAGGGCATCGGG

AAGATGGGCTTTGGAATGGTAACCCTTGGGGCCAGTGCATGGCTCATGTG

GCTTTCGGAAATTGAACCAGCCAGAATTGCATGTGTCCTCATTGTTGTGT

TTTTATTACTGGTGGTGCTCATACCCGAGCCAGAGAAGCAAAGATCTCCC

CAAGATAACCAGATGGCAATTATCATCATGGTGGCAGTGGGCCTTCTAGG

TTTGATAACTGCAAACGAACTTGGATGGCTGGAAAGAACAAAAAATGACA

TAGCTCATCTAATGGGAAGGAGAGAAGAAGGAGCAACCATGGGATTCTCA

ATGGACATTGATCTGCGGCCAGCCTCCGCCTGGGCTATCTATGCCGCATT

GACAACTCTCATCACCCCAGCTGTCCAACATGCGGTAACCACTTCATACA

ACAACTACTCCTTAATGGCGATGGCCACACAAGCTGGAGTGCTGTTTGGC

ATGGGCAAAGGGATGCCATTTTATGCATGGGACCTTGGAGTCCCGCTGCT

AATGATGGGTTGCTATTCACAATTAACACCCCTGACTCTGATAGTAGCTA

TCATTCTGCTTGTGGCGCACTACATGTACTTGATCCCAGGCCTACAAGCG

GCAGCAGCGCGTGCTGCCCAGAAAAGGACAGCAGCTGGCATCATGAAGAA

TCCCGTTGTGGATGGAATAGTGGTAACTGACATTGACACAATGACAATAG

ACCCCCAGGTGGAGAAGAAGATGGGACAAGTGTTACTCATAGCAGTAGCC

ATCTCCAGTGCTGTGCTGCTGCGGACCGCCTGGGGATGGGGGAGGCTGG

AGCTCTGATCACAGCAGCGACCTCCACCTTGTGGGAAGGCTCTCCAAACA

AATACTGGAACTCCTCTACAGCCACCTCACTGTGCAACATCTTCAGAGGA

AGCTATCTGGCAGGAGCTTCCCTTATCTATACAGTGACGAGAAACGCTGG

CCTGGTTAAGAGACGTGGAGGTGGGACGGGAGAGACTCTGGGAGAGAAGT

GGAAAGCTCGTCTGAATCAGATGTCGGCCCTGGAGTTCTACTCTTATAAA

-continued

AAGTCAGGTATCACTGAAGTGTGTAGAGAGGAGGCTCGCCGTGCCCTCAA

GGATGGAGTGGCCACAGGAGGACATGCCGTATCCCGGGGAAGTGCAAAGC

TCAGATGGTTGGTGGAGAGAGGATATCTGCAGCCCTATGGGAAGGTTGTT

GACCTCGGATGTGGCAGAGGGGGCTGGAGCTATTATGCCGCCACCATCCG

CAAAGTGCAGGAGGTGAGAGGATACACAAAGGGAGGTCCCGGTCATGAAG

AACCCATGCTGGTGCAAAGCTATGGGTGGAACATAGTTCGTCTCAAGAGT

GGAGTGGACGTCTTCCACATGGCGGCTGAGCCGTGTGACACTCTGCTGTG

TGACATAGGTGAGTCATCATCTAGTCCTGAAGTGGAAGAGACACGAACAC

TCAGAGTGCTCTCTATGGTGGGGACTGGCTTGAAAAAAGACCAGGGGCC

TTCTGTATAAAGGTGCTGTGCCCATACACCAGCACTATGATGGAAACCAT

GGAGCGACTGCAACGTAGGCATGGGGGAGGATTAGTCAGAGTGCCATTGT

CTCGCAACTCCACACATGAGATGTACTGGGTCTCTGGGGCAAAGAGCAAC

ATCATAAAAAGTGTGTCCACCACAAGTCAGCTCCTCCTGGGACGCATGGA

TGGCCCCAGGAGGCCAGTGAAATATGAGGAGGATGTGAACCTCGGCTCGG

GTACACGAGCTGTGGCAAGCTGTGCTGAGGCTCCTAACATGAAAATCATC

GGCAGGCGCATTGAGAGAATCCGCAATGAACATGCAGAAACATGGTTTCT

TGATGAAAACCACCCATACAGGACATGGGCCTACCATGGGAGCTACGAAG

CCCCCACGCAAGGATCAGCGTCTTCCCTCGTGAACGGGGTTGTTAGACTC

CTGTCAAAGCCTTGGGACGTGGTGACTGGAGTTACAGGAATAGCCATGAC

TGACACCACACCATACGGCCAACAAAGAGTCTTCAAAGAAAAAGTGGACA

CCAGGGTGCCAGATCCCCAAGAAGGCACTCGCCAGGTAATGAACATAGTC

TCTTCCTGGCTGTGGAAGGAGCTGGGGAAACGCAAGCGGCCACGCGTCTG

CACCAAAGAAGAGTTTATCAACAAGGTGCGCAGCAATGCAGCACTGGGAG

CAATATTTGAAGAGGAAAAAGAATGGAAGACGGCTGTGGAAGCTGTGAAT

GATCCAAGGTTTTGGGCCCTAGTGGATAGGGAGAGAGAACACCACCTGAG

AGGAGAGTGTCACAGCTGTGTGTACAACATGATGGGAAAAGAGAAAAGA

AGCAAGGAGAGTTCGGGAAAGCAAAAGGTAGCCGCGCCATCTGGTACATG

TGGTTGGGAGCCAGATTCTTGGAGTTTGAAGCCCTTGGATTCTTGAACGA

GGACCATTGGATGGGAAGAGAAAACTCAGGAGGTGGAGTCGAAGGGTTAG

GATTGCAAAGACTTGGATACATTCTAGAAGAAATGAATCGGGCACCAGGA

GGAAAGATGTACGCAGATGACACTGCTGGCTGGGACACCCGCATTAGTAA

GTTTGATCTGGAGAATGAAGCTCTGATTACCAACCAAATGGAGGAAGGGC

ACAGAACTCTGGCGTTGGCCGTGATTAAATACACATACCAAAACAAAGTG

GTGAAGGTTCTCAGACCAGCTGAAGGAGGAAAAACAGTTATGGACATCAT

TTCAAGACAAGACCAGAGAGGGAGTGGACAAGTTGTCACTTATGCTCTCA

ACACATTCACCAACTTGGTGGTGCAGCTTATCCGGAACATGGAAGCTGAG

GAAGTGTTAGAGATGCAAGACTTATGGTTGTTGAGGAAGCCAGAGAAAGT

GACCAGATGGTTGCAGAGCAATGGATGGGATAGACTCAAACGAATGGCGG

TCAGTGGAGATGACTGCGTTGTGAAGCCAATCGATGATAGGTTTGCACAT

GCCCTCAGGTTCTTGAATGACATGGGAAAAGTTAGGAAAGACACACAGGA

GTGGAAACCCTCGACTGGATGGAGCAATTGGGAAGAAGTCCCGTTCTGCT

CCCACCACTTCAACAAGCTGTACCTCAAGGATGGGAGATCCATTGTGGTC

CCTTGCCGCCACCAAGATGAACTGATTGGCCGAGCTCGCGTCTCACCAGG

GGCAGGATGGAGCATCCGGGAGACTGCCTGTCTTGCAAAATCATATGCGC

AGATGTGGCAGCTCCTTTATTTCCACAGAAGAGACCTTCGACTGATGGCT

AATGCCATTTGCTCGGCTGTGCCAGTTGACTGGGTACCAACTGGGAGAAC

CACCTGGTCAATCCATGGAAAGGGAGAATGGATGACCACTGAGGACATGC

TCATGGTGTGGAATAGAGTGTGGATTGAGGAGAACGACCATATGGAGGAC

AAGACTCCTGTAACAAAATGGACAGACATTCCCTATCTAGGAAAAAGGGA

GGACTTATGGTGTGGATCCCTTATAGGGCACAGACCCCGCACCACTTGGG

CTGAAAACATCAAAGACACAGTCAACATGGTGCGCAGGATCATAGGTGAT

GAAGAAAAGTACATGGACTATCTATCCACCCAAGTCCGCTACTTGGGTGA

GGAAGGGTCCACACCCGGAGTGTTGTAAGCACCAATTTTAGTGTTGTCAG

GCCTGCTAGTCAGCCACAGTTTGGGGAAAGCTGTGCAGCCTGTAACCCCC

CCAGGAGAAGCTGGGAAACCAAGCTCATAGTCAGGCCGAGAACGCCATGG

CACGGAAGAAGCCATGCTGCCTGTGAGCCCCTCAGAGGACACTGAGTCAA

AAAACCCCACGCGCTTGGAAGCGCAGGATGGGAAAAGAAGGTGGCGACCT

TCCCCACCCTTCAATCTGGGGCCTGAACTGGAGACTAGCTGTGAATCTCC

AGCAGAGGGACTAGTGGTTAGAGGAGACCCCCGGAAAACGCAAACAGC

ATATTGACGCTGGGAAAGACCAGAGACTCCATGAGTTTCCACCACGCTGG

CCGCCAGGCACAGATCGCCGAACAGCGGCGGCCGGTGTGGGGAAATCCAT

GGTTTCT

Sequences of the E gene from chimeric ZIKALIVax
virus (1512 nt; 504 aa)

SEQ ID NO: 7

ATCAGGTGCATAGGAGTCAGCAATAGGGACTTTGTGGAAGGTATGTCAGG

TGGGACTTGGGTTGATGTTGTCTTGGAACATGGAGGTTGTGTCACCGTAA

TGGCACAGGACAAACCGACTGTCGACATAGAGCTGGTTACAACAACAGTC

AGCAACATGGCGGAGGTACGATCGTACTGCTATGAGGCATCAATATCAGA

CATGGCTTCGGACAGCCGCTGCCCAACACAAGGTGAAGCCTACCTTGACA

AGCAATCAGACACTCAATATGTCTGCAAAAGAACGTTAGTGGACAGAGGC

TGGGGAAATGGATGTGGACTTTTTGGCAAAGGGAGCCTGGTGACATGCGC

TAAGTTTGCATGCTCCAAGAAAATGACCGGGAAGAGCATCCAGCCAGAGA

ATCTGGAGTACCGGATAATGCTGTCAGTTCATGGCTCCCAGCACAGTGGG

ATGACTGTCAATGATATAGGATATGAAACTGATGAGAATAGAGCGAAAGT

TGAGATAACGCCCAATTCACCAAGAGCCGAAGCCACCCTGGGGGGTTTTG

GAAGCCTAGGACTTGATTGTGAACCGAGGACAGGCCTTGACTTTTCAGAT

TTGTATTACTTGACTATGAATAACAAGCACTGGTTGGTTCACAAGGAGTG

GTTCCACGACATTCCATTACCTTGGCACGCTGGGGCAGACACCGGAACTC

CACACTGGAACAACAAAGAAGCACTGGTAGAGTTCAAGGACGCACATGCC

AAAAGGCAAACTGTCGTGGTTCTAGGGAGTCAAGAAGGAGCAGTTCACAC

GGCCCTTGCTGGAGCTCTGGAGGCTGAGATGGATGGTGCAAAGGGAAGGC

TGTCCTCTGGCCACTTGAAATGTCGCCTGAAAATGGATAAACTTAGATTG

AAGGGCGTGTCATACTCCTTGTGTACTGCAGCGTTCACATTCACCAAGAT

CCCGGCTGAAACACTGCACGGACAGTCACAGTGGAGGTACAGTACGCAG

GGACAGATGGACCTTGCAAGGTTCCAGCTCAGATGGCGGTGGACATGCAA

ACTCTGACCCCAGTTGGGAGGTTGATAACCGCTAACCCCGTAATCACTGA

AAGCACTGAGAACTCTAAGATGATGCTGGAACTTGATCCACCATTTGGGG

ACTCTTACATTGTCATAGGAGTCGGGGAGAAGAAGATCACCCACCACTGG

CACAGGAGTGGCAGCACCATTGGAAAAGCATTTGAGGCCACTGTGAGAGG

CGCCAAGAGAATGGCAGTCCTGGGGGATACAGCCTGGGACTTCGGATCAG

TCGGGGGTGTGTTCAACTCACTGGGTAAGGGCATTCACCAGATTTTTGGA

GCAGCCTTCAAATCACTGTTTGGAGGAATGTCCTGGTTCTCACAGATCCT

CATAGGCACGCTGCTAGTGTGGTTAGGTTTGAACACAAAGAATGGATCTA

TCTCCCTCACATGCTTGGCCCTGGGGGGAGTGATGATCTTCCTCTCCACG

GCTGTTTCTGCT

REFERENCES

Throughout this application, various references describe the state of the art to which this invention pertains. The disclosures of these references are hereby incorporated by reference into the present disclosure.

The invention claimed is:

1. An attenuated mutant Zika virus comprising a protein E which comprises an amino acid sequence having at least 98% identity with SEQ ID NO:1 wherein at least one amino acid residue at position 152, 156 or 158 is mutated.

2. The attenuated mutant Zika virus of claim 1 wherein the protein E comprises an amino acid sequence wherein the isoleucine residue (I) at position 152 is substituted by a threonine residue (T), the threonine residue (T) at position 156 is substituted by an isoleucine residue (I), and the histidine residue (H) at position 158 is substituted by a tyrosine residue (Y).

3. The attenuated mutant Zika virus of claim 1 wherein the protein E comprises the amino acid sequence represented by SEQ ID NO:2.

4. The attenuated mutant Zika virus of claim 1 which comprises the structural proteins C and prM of the epidemic strain and the non-structural proteins of the epidemic strain.

5. The attenuated mutant Zika virus of claim 1 which comprises the structural proteins C and prM of the epidemic strain and the non-structural proteins of the endemic strain.

6. The attenuated mutant Zika virus of claim 1, wherein the attenuated mutant Zika virus comprises a genomic sequence encoding a polyprotein comprising the amino acid sequence represented by SEQ ID NO:5.

7. The attenuated mutant Zika virus of claim 1 wherein the attenuated mutant Zika virus comprises the genomic sequence represented by SEQ ID NO:6.

8. A nucleic acid molecule encoding the attenuated mutant Zika virus of claim 1.

9. The nucleic acid molecule of claim 8 which comprises a nucleic acid sequence represented by SEQ ID NO:6.

10. A host cell comprising the nucleic acid molecule of claim 8.

11. A vaccine composition comprising the attenuated Zika virus of claim 1.

12. The vaccine composition of claim 11 wherein the attenuated Zika virus is a live attenuated Zika virus or an inactive attenuated Zika virus.

13. A method for eliciting an immune response against Zika virus in a subject comprising administering to the subject a therapeutically effective amount of the vaccine composition of claim 11.

14. The method of claim 13 wherein the subject is a pregnant woman.

15. The method of claim 13 wherein subject is a woman of childbearing age.

* * * * *